United States Patent
Mor et al.

(10) Patent No.: US 10,265,294 B2
(45) Date of Patent: Apr. 23, 2019

(54) COMPOSITIONS AND METHODS FOR TREATING EPITHELIAL CANCER

(71) Applicant: YALE UNIVERSITY, New Haven, CT (US)

(72) Inventors: Gil G. Mor, Cheshire, CT (US); Ayesha Alvero, Stratford, CT (US)

(73) Assignee: Yale University, New Haven, CT (US)

( * ) Notice: Subject to any disclaimer, the term of this patent is extended or adjusted under 35 U.S.C. 154(b) by 0 days.

(21) Appl. No.: 15/471,503

(22) Filed: Mar. 28, 2017

(65) Prior Publication Data

US 2017/0281588 A1   Oct. 5, 2017

Related U.S. Application Data

(60) Provisional application No. 62/316,109, filed on Mar. 31, 2016.

(51) Int. Cl.
*A61K 31/352* (2006.01)
*A61K 31/337* (2006.01)
(Continued)

(52) U.S. Cl.
CPC .......... *A61K 31/352* (2013.01); *A61K 31/337* (2013.01); *A61K 31/7056* (2013.01); *A61K 33/24* (2013.01); *A61K 45/06* (2013.01)

(58) Field of Classification Search
None
See application file for complete search history.

(56) References Cited

U.S. PATENT DOCUMENTS

2012/0251630 A1 * 10/2012  Alvero ................. A61K 31/353
                                                                            424/649
2016/0340329 A1    11/2016  Heaton et al.

FOREIGN PATENT DOCUMENTS

WO    2015117202 A1    8/2015

OTHER PUBLICATIONS

Alvero, et al.,"Molecular phenotyping of human ovarian cancer stem cells unravels the mechanisms for repair and chemoresistance," Cell Cycle. 8(1) ,2009 ,158-166.
(Continued)

*Primary Examiner* — Ernst V Arnold
*Assistant Examiner* — Kyung S Chang
(74) *Attorney, Agent, or Firm* — Saul Ewing Arnstein & Lehr LLP; Kathryn Doyle; Domingos J. Silva

(57) ABSTRACT

The present invention provides the eutomeric isomer of the compound of formula (I), or a salt or solvate thereof, which can be used to treat epithelial cancer in a subject. In certain embodiments, the compound of formula (I) can be used in combination with AICAR and/or cisplatin.

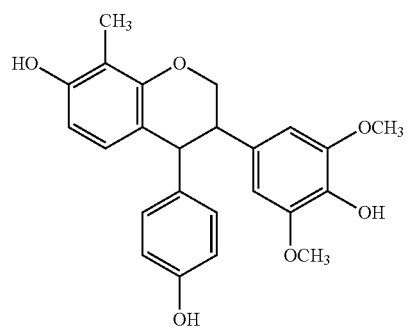

14 Claims, 26 Drawing Sheets

(51) Int. Cl.
*A61K 31/7056* (2006.01)
*A61K 33/24* (2019.01)
*A61K 45/06* (2006.01)
*A61P 35/00* (2006.01)

(56) References Cited

OTHER PUBLICATIONS

Alvero, et al.,"Targeting the mitochondria activates two independent cell death pathways in ovarian cancer stem cells," Mol Cancer Ther. 10(8) ,2011 ,1385-1393.
Chefetz, et al.,"TLR2 enhances ovarian cancer stem cell self-renewal and promotes tumor repair and recurrence," Cell Cycle 12(3) ,2013 ,511-521.
Chou, et al.,"Quantitative analysis of dose-effect relationships: the combined effects of multiple drugs or enzyme inhibitors," Adv Enzyme Regul. 22 ,1984 ,27-55 (Abstract Only).
Craveiro, et al.,"Phenotypic modifications in ovarian cancer stem cells following Paclitaxel treatment," Cancer Med. 2(6) , 2013 ,751-762.
Holford, et al.,"Understanding the dose-effect relationship: clinical application of pharmacokinetic-pharmacodynamic models," Clin Pharmacokinet. 6(6) ,1981 ,429-453.
Kamsteeg, et al.,"Phenoxodiol—an isoflavone analog—induces apoptosis in chemoresistant ovarian cancer cells," Oncogene. 22 (17) ,2003 ,2611-2620.
Loewe, et al.,"Effect of combinations: mathematical basis of the problem," Arch. Exp. Pathol. Pharmakol. 114 ,1926 ,313-326.

\* cited by examiner

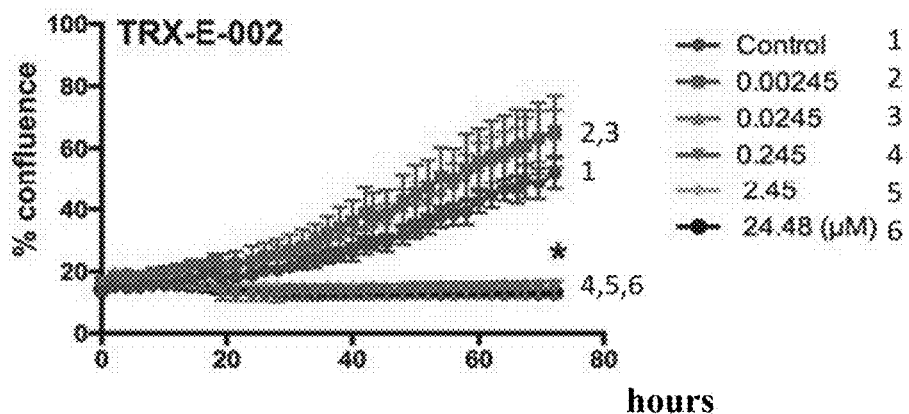
FIG. 1C
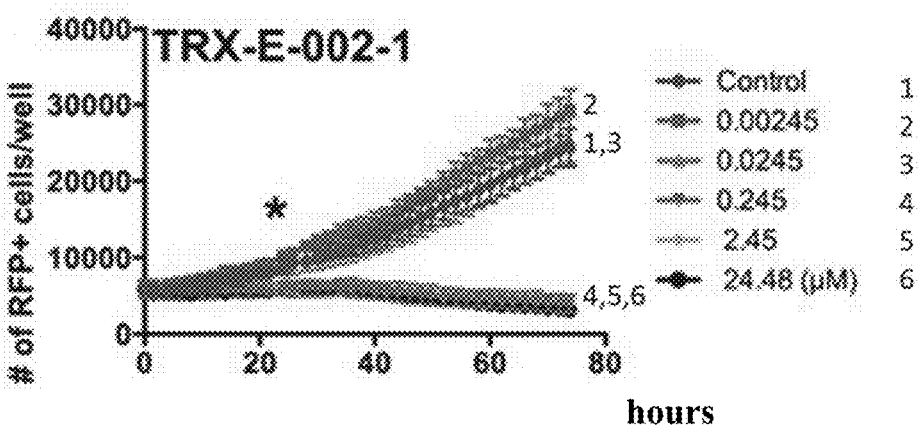
FIG. 1D
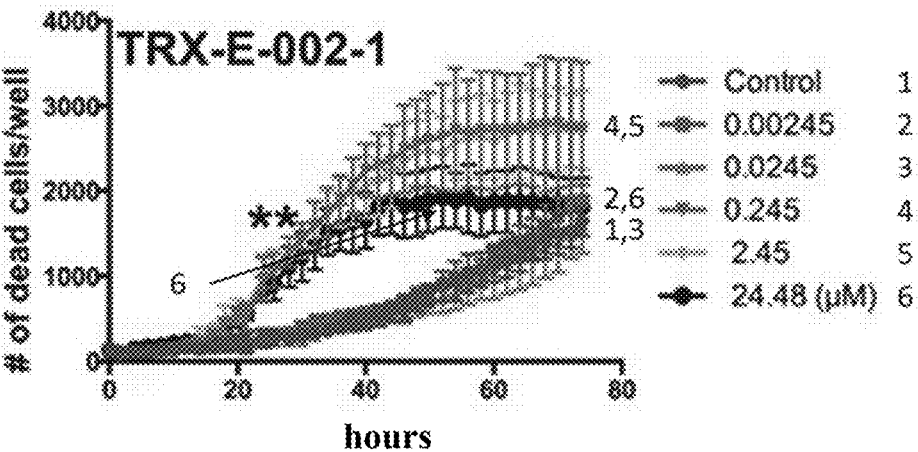

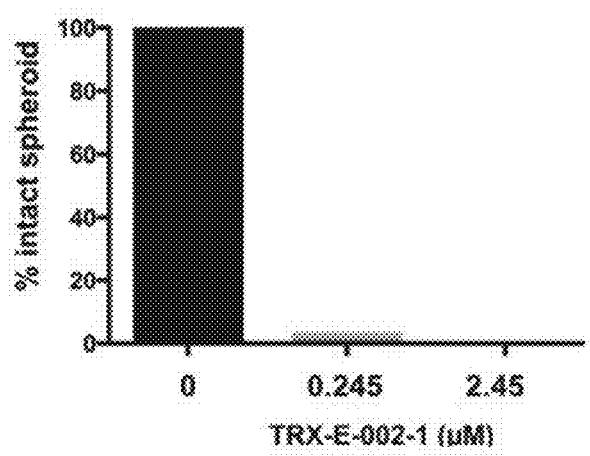
FIG. 2D

* p = 0.0013

COMPOSITIONS AND METHODS FOR TREATING EPITHELIAL CANCER

CROSS-REFERENCE TO RELATED APPLICATIONS

This application claims priority under 35 U.S.C. § 119(e) to U.S. Provisional Application No. 62/316,109, filed Mar. 31, 2016, which is incorporated herein by reference in its entirety.

BACKGROUND OF THE INVENTION

The peritoneal cavity may be affected by a number of related epithelial cancers. Such cancers are often caused by cancer stem cells (CSCs), which originate somewhere in the peritoneal cavity, including the peritoneum and the fallopian tubes, but may spread to other local organs. CSCs may be responsible for epithelial ovarian cancer, epithelial fallopian cancer, peritoneal cancer, and a wide array of carcinomas that may affect certain organs, such as the lungs, brain, breast, prostate and bowels.

Epithelial ovarian cancer is the most lethal of all gynecologic malignancies and the fourth leading cause of overall cancer deaths in women with a dismal 5-year survival rate of 45.9%. Current standard of care consists of surgical debulking and adjuvant chemotherapy with platinum and taxane, to which more than 80% of patients respond. Unfortunately, the majority of these patients eventually exhibit relapse, and upon disease recurrence the value of the standard of care is limited by the presentation of carcinomatosis and chemoresistance. As such, the majority of patients with recurrent ovarian cancer eventually succumb to the disease.

Minimal advancement in the treatment of recurrent ovarian cancer has been made in the past decade. Evidence in the literature supports the concept that tumors are complex heterogeneous organ-like systems with a hierarchical cellular organization, rather than simply as collections of homogeneous single lineage tumor cells. Ovarian tumors are heterogeneous, and inherently chemoresistant CSCs that are not removed by surgery and survive first-line chemotherapy are able to recreate the tumor and cause disease recurrence. Within the heterogeneous tumor, CD44+ ovarian cancer cells represent the chemoresistant phenotype and particularly, that the CD44+/MyD88+ ovarian cancer stem cell (OCSC) population represents the cancer cell type that can repair and rebuild the tumor. A shift in therapeutic strategy that leads to the development of unique targeted agents that attack OCSCs may enhance cancer care and prolong the survival of many patients.

There is a need in the art for methods of treating epithelial cancers, including ovarian epithelial cancer. Such methods should circumvent the chemoresistance of CSC populations after chemotherapy treatments. There is also a need in the art for methods of treating epithelial cancers, including ovarian epithelial cancer, that prevent or delay recurrence of the cancer. The present invention addresses these needs.

BRIEF SUMMARY OF THE INVENTION

The invention provides a method of treating epithelial cancer in a subject suffering from the cancer. The invention further provides pharmaceutical compositions comprising the eutomeric isomer of the compound of formula (I), or a salt or solvate thereof.

In certain embodiments, the method comprises administering to the subject in need thereof a therapeutically effective amount of the eutomeric isomer of the compound of formula (I), which is 3-(4-hydroxy-3,5-dimethoxyphenyl)-4-(4-hydroxyphenyl)-8-methylchroman-7-ol, or a salt or solvate thereof:

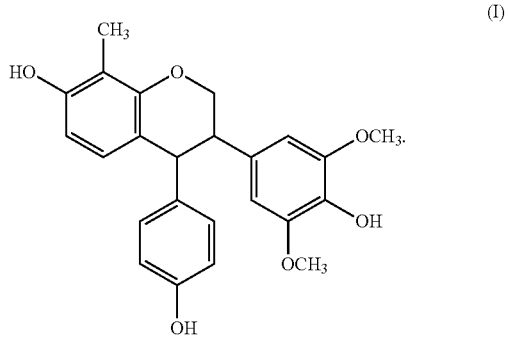 [SMILES: COc1cc(C2COc3c(ccc(O)c3C)C2c2ccc(O)cc2)cc(OC)c1O]

(I)

In certain embodiments, the compound is at least one selected from the group consisting of: (3S,4R)-3-(4-hydroxy-3,5-dimethoxyphenyl)-4-(4-hydroxyphenyl)-8-methylchroman-7-ol; (3R,4S)-3-(4-hydroxy-3,5-dimethoxyphenyl)-4-(4-hydroxyphenyl)-8-methylchroman-7-ol; (3S,4S)-3-(4-hydroxy-3,5-dimethoxyphenyl)-4-(4-hydroxyphenyl)-8-methylchroman-7-ol; and (3R,4R)-3-(4-hydroxy-3,5-dimethoxyphenyl)-4-(4-hydroxyphenyl)-8-methylchroman-7-ol.

In certain embodiments, the epithelial cancer is at least one cancer selected from the group consisting of ovarian, endometrial, pancreatic and renal.

In certain embodiments, the ovarian epithelial cancer comprises at least one selected from the group consisting of a CD44+/MyD88+ ovarian cancer stem cell and CD44−/MyD88− ovarian cancer cell.

In certain embodiments, the therapeutically effective amount of the compound ranges from about 1-1,000 mg/kg of the subject's body weight. In other embodiments, the therapeutically effective amount of the compound is about 100 mg/kg of the subject's body weight. In yet other embodiments, the therapeutically effective amount of the at least one agent ranges from about 1-500 mg/kg of the subject's body weight.

In certain embodiments, the subject is further administered a therapeutically effective amount of at least one agent selected from the group consisting of an AMPK activator, chemotherapeutic drug, or any salt, solvate, enantiomer, diastereoisomer or tautomer thereof.

In certain embodiments, the amount of the compound and the amount of the at least one agent administered to the subject are such that at least one of the following applies: (a) administration of the amount of the compound is not therapeutically effective in treating the epithelial cancer in the absence of co-administration of the amount of the at least one agent; and (b) administration of the amount of the at least one agent is not therapeutically effective in treating the epithelial cancer in the absence of co-administration of the amount of the compound.

In certain embodiments, the subject experiences an improved disease outcome when administered the compound and the at least one agent, as compared to the disease outcome when the subject is administered the compound in the absence of the at least one agent or when the subject is administered the at least one agent in the absence of the compound, wherein the disease outcome is at least one selected from the group consisting of survival rate increase, tumor size reduction, and metastatic proliferation reduction.

In certain embodiments, the chemotherapeutic drug is at least one selected from the group consisting of Paclitaxel, Cisplatin, Carboplatin, Topotican and Doxoribicin.

In certain embodiments, the AMPK activator is at least one selected from the group consisting of 5-Aminoimidazole-4-carboxamide-1-β-D-ribofuranoside (AICAR), metformin and 5-[3-[4-[2-(4-fluorophenyl)ethoxy]phenyl]propyl]-2-furancarboxylic acid.

In certain embodiments, the at least one agent is administered to the subject before the at least one compound. In other embodiments, the at least one agent is administered to the subject after the at least one compound. In yet other embodiments, the at least one agent is administered to the subject at approximately the same time as the at least one compound. In yet other embodiments, the at least one agent is administered to the subject at the same time as the at least one compound. In yet other embodiments, the at least one agent is coformulated with the at least one compound.

In certain embodiments, the subject is administered the compound as part of a maintenance treatment after having been treated with at least one chemotherapy.

In certain embodiments, the subject has suffered at least one epithelial cancer recurrence.

In certain embodiments, the epithelial cancer recurrence is an ovarian cancer recurrence.

In certain embodiments, the compound is administered to the subject once per day, and every week day.

In certain embodiments, the compound is administered to the subject once per day, and five days out of every seven week days, with two consecutive rest days wherein the compound is not administered to the subject.

In certain embodiments, the maintenance treatment prevents or delays in the subject at least one selected from the group consisting of epithelial cancer recurrence and epithelial cancer metastasis.

In certain embodiments, the compound is formulated in a pharmaceutical composition as part of a nanoparticle, which is optionally coated with a peptide comprising ArgGlyAsp.

In certain embodiments, the epithelial cancer is at least one selected from the group consisting of recurring and resistant to at least one chemotherapy.

In certain embodiments, the pharmaceutical composition comprises an amount of the eutomeric isomer of the compound of formula (I), or a salt or solvate thereof. In other embodiments, the pharmaceutical composition comprises an amount of at least one agent selected from the group consisting of an AMPK activator, chemotherapeutic drug, or a salt or solvate thereof. In yet other embodiments, administration of the composition to a subject suffering from epithelial cancer treats or prevents the cancer. In yet other embodiments, the subject is female and suffering from ovarian cancer.

In certain embodiments, the amount of the compound and the amount of the at least one agent in the composition are such that at least one of the following applies: (a) administration of the amount of the compound in the composition is not therapeutically effective in treating the epithelial cancer in the absence of the co-administration of the amount of at least one agent in the composition; and (b) administration of the amount of the at least one agent in the composition is not therapeutically effective in treating the epithelial cancer in the absence of co-administration of the amount of the compound in the composition.

In certain embodiments, the subject experiences an improved disease outcome when administered the pharmaceutical composition, as compared to the disease outcome when the subject is administered the amount of the compound in the absence of the amount of the at least one agent or when the subject is administered the amount of the at least one agent in the absence of the amount of the compound, wherein the disease outcome is at least one selected from the group consisting of survival rate increase, tumor size reduction, and metastatic proliferation reduction.

BRIEF DESCRIPTION OF THE DRAWINGS

For the purpose of illustrating the invention, there are depicted in the drawings certain embodiments of the invention. However, the invention is not limited to the precise arrangements and instrumentalities of the embodiments depicted in the drawings.

FIGS. 1A-1G illustrate findings that TRX-E-002-1 demonstrates superior potency against chemoresistant ovarian cancer stem cells as compared to the current standard care treatments as well as its own enantiomer. FIG. 1A illustrates a panel of SBP (super-benzopyran) analogs from three subfamilies screened against two clones of chemoresistant CD44+/MyD88+ OCSCs. $IC_{50}$ values for both clones are plotted. FIG. 1B illustrates the cellular morphology of OCSCs exposed to treatment with cisplatin, paclitaxel and TRX-E-002 for 24 hours. FIG. 1C illustrates the cell growth of OCSCs exposed to increasing concentrations of TRX-E-002; note the significant decrease in cell growth at higher concentrations. FIGS. 1D-1E demonstrate the difference in activity against OCSCs of the TRX-E-002 enantiomers, TRX-E-002-1 and TRX-E-002-2. FIG. 1D illustrates the much higher activity of the TRX-E-002-1 enantiomer over the TRX-E-002-2 enantiomer (FIG. 1E) in terms of both the number of RFP+ cells and number of dead/Celltox-positive cells. FIG. 1F illustrates a morphological analysis of OCSCs exposed to TRX-E-002-1 and TRX-E-002-2 and the calculation of $IC_{50}$ values for both TRX-E-002-1 and TRX-E-002-2. FIG. 1G illustrates a graph of the activity of TRX-E-002-1 and TRX-E-002-2 against OCSC2 line at 24 hours, demonstrating the higher activity of the TRX-E-002-1 enantiomer. *p=0.0332 for 0.245 μM at 21 hr; **p=0.0101 for 0.245 μM at 24 hr.

FIGS. 2A-2E illustrate findings that TRX-E-002-1 is active against in vitro models of ovarian cancer cells. FIG. 2A: TRX-E-002-1 efficacy was tested against two clones of chemosensitive CD44−/MyD88− OCCs. The $IC_{50}$ was calculated to be at the nM range; mCherry+OCSC2 and GFP+OCC2 were co-cultured at 50/50 and treated with TRX-E-002-1 (0.12 μM), Cisplatin (20 μM), or the combination. FIG. 2B illustrates a morphological analysis of cultures of mCherry+OCSC2 and GFP+OCC2 at 50/50 and treated with TRX-E-002-1 (0.12 μM), Cisplatin (20 μM), or the combination. FIG. 2C illustrates the quantification of cell numbers showing that TRX-E-002-1 is able to induce cell death in both mCherry+OCSC2 and GFP+OCC2 cell types. Data are presented as the effect of the treatments on each cell type differentiated by the fluorescent count. FIG. 2D illustrates that spheroids are formed from GFP-expressing OCSCs and treated with TRX-E-002-1; that Figure illustrates the quantification of intact spheroids and also depicts phase contrast images showing spheroid integrity/collapse. FIG. 2E depicts composite images of control and TRX-E-002-1 treated OCSC spheroids through time; note the collapse of the outer ring on the TRX-E-002-1 treated spheroids.

FIG. 3A illustrates OCSCs that were treated with TRX-E-002-1 (2.45

μM) or Cisplatin (2 μM) for 24 hours and allowed to recover in fresh growth media for another 48 hours. In contrast to Cisplatin, TRX-E-002-1 treatment prevented recovery of OCSCs. FIG. 3B depicts a composite image of OCSCs after 24 hours of treatment and subsequent recovery. FIG. 3C: OCSCs were treated with increasing concentrations of TRX-E-002-1 for 2 hours and allowed to recover in fresh growth media for another 48 hours. Treatment with 2.45 μM TRX-E-002-1 for only 2 hours induced a sustained cytotoxic effect. FIG. 3D depicts a composite image of OCSCs after 2 hours of treatment and subsequent recovery.

FIG. 4A depicts Western blot analyses for phosphorylated and total forms of c-Jun and ERK in OCSCs treated with 0.2 TRX-E-002-1 at designated time points. FIG. 4B depicts Western blot analyses wherein OCSCs treated with either 0.245 μM or 2.45 μM TRX-E-002-1 for 2 hours followed by removal of the treatment and recovery in fresh growth media. Cells were collected at designated time-points. Sustained increase in p-c-Jun depicted in FIG. 4B correlated with inhibition of recovery depicted in FIG. 3C. FIG. 4C depicts Western blot analyses wherein OCSCs were pretreated for 30 mins with SP600125 (1,9-pyrazoloanthrone; 10 μM) prior to adding TRX-E-002-1 (0.2 μM). Samples were collected 2 hours after treatment and p-c-Jun and p-ERK levels were determined by western blot analysis. FIG. 4D depicts Western blot analyses wherein OCSCs were treated with ERK inhibitor, U0126 (1,4-diamino-2,3-dicyano-1,4-bis(2-aminophenylthio)butadiene; 10 μM), or TRX-E-002-1 (0.2 μM) for 2 hours. Samples were collected 2 hours after treatment and p-c-Jun and p-ERK levels were determined by western blot analysis. FIGS. 4E-4F illustrates graphs comparing the results of the experiments depicted in FIGS. 4C-4D run in parallel to determine effect on cell death at 24 hour time-point. FIG. 4E: C, control; SP, SP600125 (10 μM), TRX, TRX-E-002-1 (0.2 μM). FIG. 4F: C, control; U, U0126 (10 μM); TRX, TRX-E-002-1 (0.2 μM).

FIGS. 5A-5B: OCSCs were treated with 0.245 μM TRX-E-002-1; samples were collected at designated time-points and caspase-3 and caspase-9 activity was quantified by Caspase Glo assay. *p<0.0001 compared to no treatment control. FIG. 5C illustrates Western blot analyses wherein OCSCs were transiently transfected with scramble siRNA or specific siRNA for c-Jun, treated with 2.45 μM TRX-E-002-1 for 2 hours and allowed to recover in growth media at designated time-points. TRX-E-002-1-induced increase in levels of total and p-c-Jun is lower in cells transfected with siRNA for c-Jun; this correlates with the absence of active caspase-3.

FIGS. 6A-6F: Treatment of primary disease: Once tumors were detected by live imagine, mice were treated i.p. with 50 mg/kg or 100 mg/kg TRX-E-002-1 daily. FIG. 6A illustrates tumor growth curves as measured using mCherry fluorescence area. FIG. 6B illustrates quantification of total i.p. tumor burden at the end of the study. FIG. 6C illustrates quantification of the percentage of body weight lost or gained by the end of the study, * p=0.0147. FIG. 6D illustrates quantification of white blood cell count per liter, p>0.05. FIG. 6E depicts representative images showing mCherry+tumors. FIG. 6F depicts Western blot analyses for p-c-Jun and total c-Jun in residual tumors from C, control mice, or T, mice treated with TRX-E-002-1 (100 mg/kg). Representative Western blot from two controls and two TRX-E-002-1 treated mice are presented. FIG. 6G: Combination treatment with TRX-E-002-1 and Cisplatin: In parallel experiments, mice were treated with Cisplatin (3 doses at 5 mg/kg given weekly), TRX-E-002-1 (16 doses at 100 mg/kg given daily), or the combination of both. Percentage of surviving animals was reported at day 47. FIGS. 6H-6J: Treatment of recurrent disease: Once tumors were established and detected by live imaging, mice were treated with Paclitaxel (4 doses at 12 mg/kg) then re-randomized to designated maintenance treatments. FIG. 6H depicts representative images showing mCherry+tumors. FIG. 6I depicts tumor growth curves during the $1^{st}$ line treatment with Paclitaxel (left hand portion of the graph) and maintenance treatment (right hand portion of the graph). Legend: 1=no treatment control, 2=Paclitaxel, maintenance with vehicle, 3=Paclitaxel, maintenance with Paclitaxel, 4=Paclitaxel, maintenance with TRX-E-002-1. FIG. 6J illustrates quantification of total i.p. tumor burden at the end of the study and depicts images of representative mice. *p=0.0029 and p<0.0001, control vs. 50 mg/kg or 100 mg/kg, respectively; **p<0.0001, control vs. both doses; +p<0.0001, control vs $1^{st}$ line Paclitaxel; ++p<0.0001, TRX-E-002-1 maintenance vs Paclitaxel maintenance.

FIG. 7A-7F: Once tumors were detected by live imaging, mice were treated i.p. with 150 mg/kg TRX-E-002-1 three times weekly. FIG. 7A illustrates tumor growth curves as measured using mCherry fluorescence area, * p<0.0001. FIG. 7B illustrates quantification of total i.p. tumor burden at the end of the study, * p=0.1245. FIG. 7C illustrates quantification of the percentage of body weight lost or gained by the end of the study, * p=0.0013. FIG. 7D illustrates quantification of white blood cells per liter, * p<0.001. FIG. 7E illustrates quantification of the neutrophil count at the end of the study. FIG. 7F illustrates quantification of the lymphocyte count at the end of the study.

DETAILED DESCRIPTION OF THE INVENTION

Figure 1A:
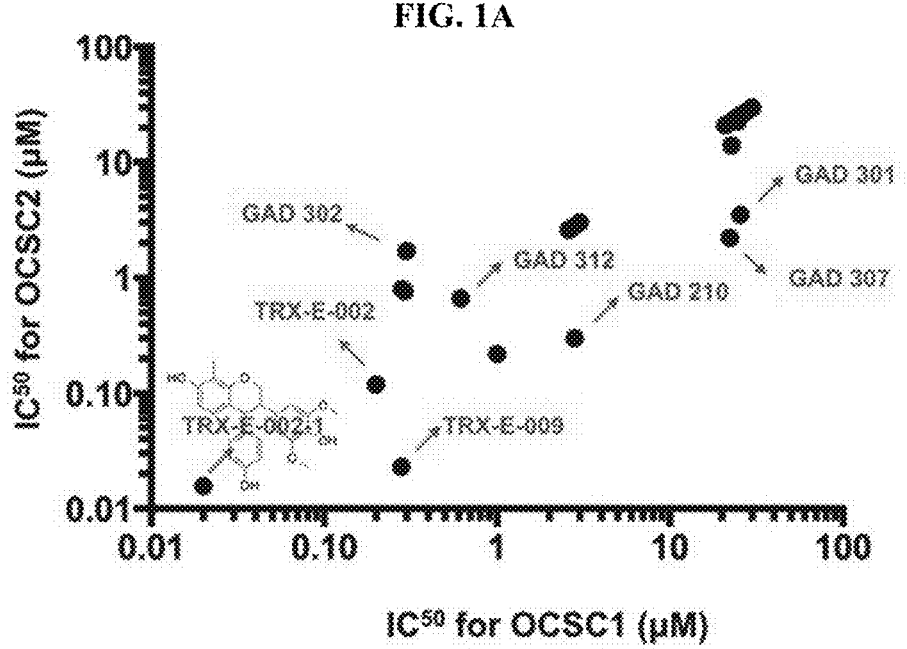

The invention relates in certain aspects to the unexpected discovery that compound TRX-E-002-1 can be used to treat epithelial cancer. In certain embodiments, TRX-E-002-1 inhibits or hampers growth of CD44+/MyD88+ epithelial cancer stem cells (CSCs), including ovarian cancer stem cells (OCSCs). In other embodiments, TRX-E-002-1 induces cell death of and/or kills CSCs. In yet other embodiments, the CSCs are chemoresistant. In yet other embodiments, TRX-E-002-1 is used in combination with cisplatin.

The invention relates in other aspects to the unexpected discovery that TRX-E-002-1 can be used in combination with a AMP-dependent protein kinase (AMPK) activator to treat chemoresistant epithelial cancer stem cells and/or prevent or hamper recurrence of such cells. In certain embodiments, the AMPK activator comprises AICAR (5-Aminoimidazole-4-carboxamide-1-β-D-ribofuranoside, or a salt thereof).

The present invention includes methods of treating epithelial cancer in a patient. In certain embodiments, invention includes methods of treating ovarian epithelial cancer in a female patient. In other embodiments, the ovarian epithelial cancer is a recurring cancer. In yet other embodiments, the cancer is chemoresistant cancer. The present invention further includes methods of preventing or delaying the recurrence of ovarian epithelial cancer in a female patient.

Flavanoids are a group of polyphenol compounds found in plants that are characterized by a benzo-gamma-pyrone structure and induce mitotic arrest and apoptosis. As demonstrated herein, one specific SBP analog, TRX-E-002-1, was found to have exceptional anti-tumor activity by inducing cell death in CSCs.

Definitions

Unless defined otherwise, all technical and scientific terms used herein have the same meaning as commonly understood by one of ordinary skill in the art to which this invention belongs. Although any methods and materials similar or equivalent to those described herein can be used in the practice or testing of the present invention, exemplary methods and materials are described. As used herein, each of the following terms has the meaning associated with it in this section.

Generally, the nomenclature used herein and the laboratory procedures in cell culture, oncology, molecular genetics, pharmacology and organic chemistry are those well-known and commonly employed in the art.

Standard techniques are used for biochemical and/or biological manipulations. The techniques and procedures are generally performed according to conventional methods in the art and various general references (e.g., Sambrook and Russell, 2012, Molecular Cloning, A Laboratory Approach, Cold Spring Harbor Press, Cold Spring Harbor, N.Y., and Ausubel et al., 2002, Current Protocols in Molecular Biology, John Wiley & Sons, NY), which are provided throughout this document.

The articles "a" and "an" are used herein to refer to one or to more than one (i.e., to at least one) of the grammatical object of the article. By way of example, "an element" means one element or more than one element.

"About" as used herein when referring to a measurable value such as an amount, a temporal duration, and the like, is meant to encompass variations of ±20% or ±10%, more preferably ±5%, even more preferably ±1%, and still more preferably ±0.1% from the specified value, as such variations are appropriate to perform the disclosed methods.

As used herein, the terms "analog," "analogue," or "derivative" are meant to refer to a chemical compound or molecule prepared from another compound or molecule by one or more chemical reactions. As such, an analog can be a structure similar to, or based on, the structure of any small molecule inhibitor described herein, and/or may have a similar or dissimilar metabolic behavior.

The term "apoptosis," as used herein, means an active process, involving the activation of a preexisting cellular pathway, induced by an extracellular or intracellular signal, causing the natural programmed death of the cell. In particular, the cell death involves nuclear fragmentation, chromatin condensation, and the like, in a cell with an intact membrane.

An "apoptosis-inducing agent" refers to an agent that inhibits cancer-cell proliferation or tumor growth, at least in part, by inducing apoptosis or programmed cell death in cancer cells.

The term "cancer" as used herein is defined as disease characterized by the rapid and uncontrolled growth of aberrant cells. Cancer cells can spread locally or through the bloodstream and lymphatic system to other parts of the body. Examples of various cancers include but are not limited to, breast cancer, prostate cancer, ovarian cancer, cervical cancer, skin cancer, pancreatic cancer, colorectal cancer, renal cancer, liver cancer, brain cancer, lymphoma, leukemia, lung cancer and the like. In some instances, hyperproliferative disorders are referred to as a type of cancer including but not limited to primary or metastatic melanoma, thymoma, lymphoma, sarcoma, lung cancer, liver cancer, non-Hodgkin's lymphoma, Hodgkins lymphoma, leukemias, uterine cancer, cervical cancer, bladder cancer, kidney cancer and adenocarcinomas such as breast cancer, prostate cancer, ovarian cancer, pancreatic cancer, and the like.

The term "cancer stem cells" or "CSCs" as used herein refers to cancer cells that possess characteristics associated with normal stem cells, specifically the ability to give rise to all cell types found in a particular cancer sample. CSCs are therefore tumorigenic, in contrast to other non-tumorigenic cancer cells. CSCs may generate tumors through the stem cell processes of self-renewal and differentiation into multiple cell types. Such cells are resistant to chemotherapy and may persist in tumors as a distinct population and cause relapse and metastasis by giving rise to new tumors.

A "disease" is a state of health of an animal wherein the animal cannot maintain homeostasis, and wherein if the disease is not ameliorated then the animal's health continues to deteriorate. In contrast, a "disorder" in an animal is a state of health in which the animal is able to maintain homeostasis, but in which the animal's state of health is less favorable than it would be in the absence of the disorder. Left untreated, a disorder does not necessarily cause a further decrease in the animal's state of health.

As used herein, the term "eutomer" or "eutomeric" refers to the chiral enantiomer and/or diastereoisomer having the desired pharmacological activity, e.g., as an active ingredient in a drug. In contrast, the term "distomer" or "distomeric" refers to the enantiomer and/or diastereoisomer of the eutomer that has undesired bioactivity or may be bio-inert. Armed with the structure of a compound comprising at least one chiral center, and with the appropriate biochemical and/or biological protocols disclosed herein and/or known in the art, one skilled in the art will be able to separate and characterize the enantiomers and/or diastereoisomers of the compound, including its eutomer(s) and/or the distomer(s), through routine experimentation.

As used herein, a composition of component A that is "essentially free" of component B has a component A/component B ratio of about 75:25, 80:20, 85:15, 90:10; 92.5:7.5; 95:5, 96:4, 97:3, 98:2, 99:1, 99.5:0.5, 99.6:0.4, 99.7:0.3, 99.8:0.2, 99.9:0.1, 99.95:0.05, 99.99:0.01, 99.995:0.005, 99.999:0.001, 100:0, or any fraction or multiple thereof.

The phrase "inhibit," as used herein, means to reduce a molecule, a reaction, an interaction, a gene, an mRNA, and/or a protein's expression, stability, function or activity by a measurable amount or to prevent entirely. Inhibitors are compounds that, e.g., bind to, partially or totally block stimulation, decrease, prevent, delay activation, inactivate, desensitize, or down regulate a protein, a gene, and an mRNA stability, expression, function and activity, e.g., antagonists.

As used herein, the term "maintenance treatment" or "maintenance therapy" refers to a medical treatment usually administered after the primary treatment, and may comprise of one or more additional treatments over a period of time. Maintenance treatments may be administered continuously or only "as needed" based on the guidance of a medical professional. Maintenance treatments may act to prevent the recurrence of a disease or disorder or to prolong remission of a disease or disorder.

As used herein, the term "pharmaceutical composition" or "composition" refers to a mixture of at least one compound useful within the invention with a pharmaceutically acceptable carrier. The pharmaceutical composition facilitates administration of the compound to a subject.

As used herein, the term "pharmaceutically acceptable carrier" means a pharmaceutically acceptable material, composition or carrier, such as a liquid or solid filler, stabilizer, dispersing agent, suspending agent, diluent, excipient, thickening agent, solvent or encapsulating material, involved in carrying or transporting a compound useful within the invention within or to the patient such that it may perform its intended function. Typically, such constructs are carried or transported from one organ, or portion of the body, to another organ, or portion of the body. Each carrier must be "acceptable" in the sense of being compatible with the other ingredients of the formulation, including the compound useful within the invention, and not injurious to the patient. Some examples of materials that may serve as pharmaceutically acceptable carriers include: sugars, such as lactose, glucose and sucrose; starches, such as corn starch and potato starch; cellulose, and its derivatives, such as sodium carboxymethyl cellulose, ethyl cellulose and cellulose acetate; powdered tragacanth; malt; gelatin; talc; excipients, such as cocoa butter and suppository waxes; oils, such as peanut oil, cottonseed oil, safflower oil, sesame oil, olive oil, corn oil and soybean oil; glycols, such as propylene glycol; polyols, such as glycerin, sorbitol, mannitol and polyethylene glycol; esters, such as ethyl oleate and ethyl laurate; agar; buffering agents, such as magnesium hydroxide and aluminum hydroxide; surface active agents; alginic acid; pyrogen-free water; isotonic saline; Ringer's solution; ethyl alcohol; phosphate buffer solutions; and other non-toxic compatible substances employed in pharmaceutical formulations. As used herein, "pharmaceutically acceptable carrier" also includes any and all coatings, antibacterial and antifungal agents, and absorption delaying agents, and the like that are compatible with the activity of the compound useful within the invention, and are physiologically acceptable to the patient. Supplementary active compounds may also be incorporated into the compositions. The "pharmaceutically acceptable carrier" may further include a pharmaceutically acceptable salt of the compound useful within the invention. Other additional ingredients that may be included in the pharmaceutical compositions used in the practice of the invention are known in the art and described, for example in Remington's Pharmaceutical Sciences (Genaro, Ed., Mack Publishing Co., 1985, Easton, Pa.), which is incorporated herein by reference.

As used herein, the language "pharmaceutically acceptable salt" refers to a salt of the administered compound prepared from pharmaceutically acceptable non-toxic acids and bases, including inorganic acids, inorganic bases, organic acids, inorganic bases, solvates, hydrates, and clathrates thereof. Suitable pharmaceutically acceptable acid addition salts may be prepared from an inorganic acid or from an organic acid. Examples of inorganic acids include sulfate, hydrogen sulfate, hydrochloric, hydrobromic, hydriodic, nitric, carbonic, sulfuric, and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid. Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (N-methylglucamine) and procaine. All of these salts may be prepared from the corresponding compound by reacting, for example, the appropriate acid or base with the compound.

The terms "pharmaceutically effective amount" and "effective amount" refer to a nontoxic but sufficient amount of an agent to provide the desired biological result. That result can be reduction and/or alleviation of the signs, symptoms, or causes of a disease or disorder, or any other desired alteration of a biological system. An appropriate effective amount in any individual case may be determined by one of ordinary skill in the art using routine experimentation. By "pharmaceutical formulation" it is further meant that the carrier, solvent, excipient(s) and/or salt must be compatible with the active ingredient of the formulation (e.g. a compound of the invention). It is understood by those of ordinary skill in this art that the terms "pharmaceutical formulation" and "pharmaceutical composition" are generally interchangeable, and they are so used for the purposes of this application.

As used herein, the term "prevent," "prevention," or "preventing" refers to any method to partially or completely prevent or delay the onset of one or more symptoms or features of a disease, disorder, and/or condition. Prevention is causing the clinical symptoms of the disease state not to develop, i.e., inhibiting the onset of disease, in a subject that may be exposed to or predisposed to the disease state, but does not yet experience or display symptoms of the disease state. Prevention may be administered to a subject who does not exhibit signs of a disease, disorder, and/or condition.

As used herein, the term "subject," "patient" or "individual" to which administration is contemplated includes, but is not limited to, humans (i.e., a male or female of any age group, e.g., a pediatric subject (e.g., infant, child, adolescent) or adult subject (e.g., young adult, middle-aged adult or senior adult)) and/or other primates (e.g., cynomolgus monkeys, rhesus monkeys); mammals, including commercially relevant mammals such as cattle, pigs, horses, sheep, goats, cats, and/or dogs; and/or birds, including commercially relevant birds such as chickens, ducks, geese, quail, and/or turkeys.

As used herein, the term "therapeutically effective amount" is an amount of a compound of the invention, that when administered to a patient, treats, minimizes and/or ameliorates a symptom of the disease or disorder. The amount of a compound of the invention that constitutes a "therapeutically effective amount" will vary depending on the compound, the disease state and its severity, the age of the patient to be treated, and the like. The therapeutically effective amount can be determined routinely by one of ordinary skill in the art having regard to his own knowledge and to this disclosure.

The terms "treat," "treating," and "treatment," refer to therapeutic or preventative measures described herein. The methods of "treatment" employ administration to a subject, in need of such treatment, a composition of the present invention, for example, a subject afflicted a disease or disorder, or a subject who ultimately may acquire such a disease or disorder, in order to prevent, cure, delay, reduce the severity of, or ameliorate one or more symptoms of the disorder or recurring disorder, or in order to prolong the survival of a subject beyond that expected in the absence of such treatment.

Ranges: throughout this disclosure, various aspects of the invention can be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following abbreviations are used herein: AICAR, 5-aminoimidazole-4-carboxamide-1-β-D-ribofuranoside, or a salt thereof; AMP, Adenosine monophosphate, or a salt thereof; AMPK, adenosine monophosphate-activated protein kinase; ERK, extracellular-signal-regulated kinases; GAPDH, glyceraldehyde 3-phosphatase dehydrogenase; GFP, green fluorescent protein; i.p., intraperitoneal; MTD, maximum tolerated dose; OCC, ovarian cancer cells; OCSC, ovarian cancer stem cells; RFP, red fluorescent protein; SBP, super-benzopyran; siRNA, small interfering RNA; SFC, supercritical fluid chromatography.

Compounds and Compositions

The present invention relates to the compound of formula (I), also known as 3-(4-hydroxy-3,5-dimethoxyphenyl)-4-(4-hydroxyphenyl)-8-methylchroman-7-ol, or a salt or solvate thereof, as well as compositions comprising the same:

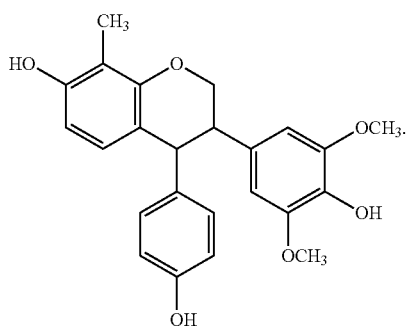

(I)

The present invention further relates to the eutomeric isomer (such as, but not limited to, enantiomer or diastereoisomer) of the compound of formula (I), or a salt or solvate thereof, as well as compositions comprising the same.

In certain embodiments, the compound is (3S,4R)-3-(4-hydroxy-3,5-dimethoxyphenyl)-4-(4-hydroxyphenyl)-8-methylchroman-7-ol, or a salt or solvate thereof:

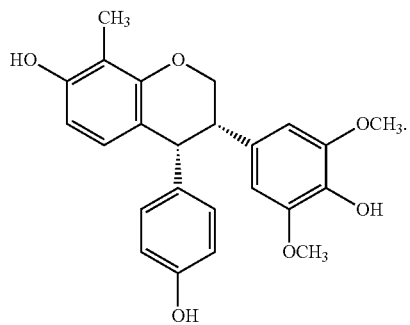 [SMILES: COc1cc([C@H]2COc3c(ccc(O)c3C)[C@H]2c2ccc(O)cc2)cc(OC)c1O]

In certain embodiments, the compound is (3R,4S)-3-(4-hydroxy-3,5-dimethoxyphenyl)-4-(4-hydroxyphenyl)-8-methylchroman-7-ol, or a salt or solvate thereof:

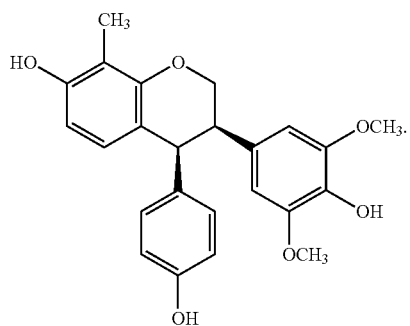 [SMILES: COc1cc([C@@H]2COc3c(ccc(O)c3C)[C@@H]2c2ccc(O)cc2)cc(OC)c1O]

In certain embodiments, the compound is (3S,4S)-3-(4-hydroxy-3,5-dimethoxyphenyl)-4-(4-hydroxyphenyl)-8-methylchroman-7-ol, or a salt or solvate thereof:

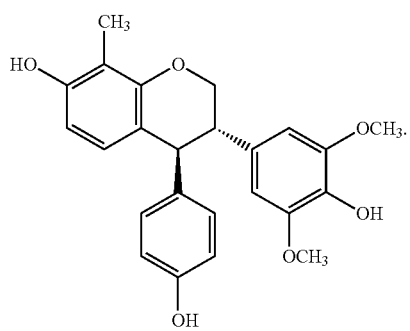 [SMILES: COc1cc([C@H]2COc3c(ccc(O)c3C)[C@@H]2c2ccc(O)cc2)cc(OC)c1O]

In certain embodiments, the compound is (3R,4R)-3-(4-hydroxy-3,5-dimethoxyphenyl)-4-(4-hydroxyphenyl)-8-methylchroman-7-ol, or a salt or solvate thereof:

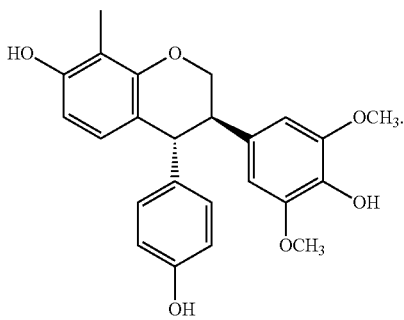 [SMILES: COc1cc([C@@H]2COc3c(ccc(O)c3C)[C@H]2c2ccc(O)cc2)cc(OC)c1O]

In certain embodiments, the mixture of the compound and its corresponding enantiomer and/or diastereoisomer is obtained using the procedure outlined in WO2015117202 and/or US20160340329.

In certain embodiments, the compound has a shorter retention time in a normal phase Chiralcel OD-H, 30×250 mm, 5μ column, than its corresponding enantiomer and/or diastereoisomer. In other embodiments, the compound has a longer retention time in a normal phase Chiralcel OD-H, 30×250 mm, 5μ column, than its corresponding enantiomer and/or diastereoisomer.

In certain embodiments, the compound has positive optical rotation $[\alpha]^{25}_{589}$ in methanol. In other embodiments, the compound has $[\alpha]^{25}_{589}=+(277\text{-}282°)$ in methanol (1.0%).

In certain embodiments, the compound has negative optical rotation $[\alpha]^{25}_{589}$ in methanol. In other embodiments, the compound has $[\alpha]^{25}_{589}=-(277\text{-}282°)$ in methanol (1.0%).

In certain embodiments, the compound is (3S,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of (3R,4S)-3-(4-hydroxy-3,5-dimethoxyphenyl)-4-(4-hydroxyphenyl)-8-methylchroman-7-ol, or a salt or solvate thereof.

In certain embodiments, the compound is (3R,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of (3S,4R)-3-(4-hydroxy-3,5-dimethoxyphenyl)-4-(4-hydroxyphenyl)-8-methylchroman-7-ol, or a salt or solvate thereof.

In certain embodiments, the compound is (3S,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of (3R,4R)-3-(4-hydroxy-3,5-dimethoxyphenyl)-4-(4-hydroxyphenyl)-8-methylchroman-7-ol, or a salt or solvate thereof.

In certain embodiments, the compound is (3R,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of (3S,4S)-3-(4-hydroxy-3,5-dimethoxyphenyl)-4-(4-hydroxyphenyl)-8-methylchroman-7-ol, or a salt or solvate thereof.

In certain embodiments, the compound is (3S,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of at least one selected from the group consisting of (3R,4S)-3-(4-hydroxy-3,5-dimethoxyphenyl)-4-(4-hydroxyphenyl)-8-methylchroman-7-ol, (3R,4R)-3-(4-hydroxy-3,5-dimethoxyphenyl)-4-(4-hydroxyphenyl)-8-methylchroman-7-ol, (3S,4S)-3-(4-hydroxy-3,5-dimethoxyphenyl)-4-(4-hydroxyphenyl)-8-methylchroman-7-ol, or a salt or solvate thereof.

In certain embodiments, the compound is (3R,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of at least one selected from the group consisting of (3S,4R)-3-(4-hydroxy-3,5-dimethoxyphenyl)-4-(4-hydroxyphenyl)-8-methylchroman-7-ol, (3R,4S)-3-(4-hydroxy-3,5-dimethoxyphenyl)-4-(4-hydroxyphenyl)-8-methylchroman-7-ol, (3S,4R)-3-(4-hydroxy-3,5-dimethoxyphenyl)-4-(4-hydroxyphenyl)-8-methylchroman-7-ol, or a salt or solvate thereof.

In certain embodiments, the compound is (3S,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of at least one selected from the group consisting of (3R,4R)-3-(4-hydroxy-3,5-dimethoxyphenyl)-4-(4-hydroxyphenyl)-8-methylchroman-7-ol, (3R,4S)-3-(4-hydroxy-3,5-dimethoxyphenyl)-4-(4-hydroxyphenyl)-8-methylchroman-7-ol, (3S,4R)-3-(4-hydroxy-3,5-dimethoxyphenyl)-4-(4-hydroxyphenyl)-8-methylchroman-7-ol, or a salt or solvate thereof.

In certain embodiments, the compound is (3R,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of at least one selected from the group consisting of (3S,4S)-3-(4-hydroxy-3,5-dimethoxyphenyl)-4-(4-hydroxyphenyl)-8-methylchroman-7-ol, (3R,4S)-3-(4-hydroxy-3,5-dimethoxyphenyl)-4-(4-hydroxyphenyl)-8-methylchroman-7-ol, (3S,4R)-3-(4-hydroxy-3,5-dimethoxyphenyl)-4-(4-hydroxyphenyl)-8-methylchroman-7-ol, or a salt or solvate thereof.

In certain embodiments, the compound is (3S,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of each one selected from the group consisting of (3R,4S)-3-(4-hydroxy-3,5-dimethoxyphenyl)-4-(4-hydroxyphenyl)-8-methylchroman-7-ol, (3R,4R)-3-(4-hydroxy-3,5-dimethoxyphenyl)-4-(4-hydroxyphenyl)-8-methylchroman-7-ol, (3S,4S)-3-(4-hydroxy-3,5-dimethoxyphenyl)-4-(4-hydroxyphenyl)-8-methylchroman-7-ol, or a salt or solvate thereof.

In certain embodiments, the compound is (3R,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of each one selected from the group consisting of (3S,4R)-3-(4-hydroxy-3,5-dimethoxyphenyl)-4-(4-hydroxyphenyl)-8-methylchroman-7-ol, (3R,4R)-3-(4-hydroxy-3,5-dimethoxyphenyl)-4-(4-hydroxyphenyl)-8-methylchroman-7-ol, (3S,4S)-3-(4-hydroxy-3,5-dimethoxyphenyl)-4-(4-hydroxyphenyl)-8-methylchroman-7-ol, or a salt or solvate thereof.

In certain embodiments, the compound is (3S,4S)-3-(4-hydroxy-3,5-dimethoxyphenyl)-4-(4-hydroxyphenyl)-8-methylchroman-7-ol, or a salt or solvate thereof, which is in a composition that is free, or essentially free, of each one selected from the group consisting of (3R,4R)-3-(4-hydroxy-3,5-dimethoxyphenyl)-4-(4-hydroxyphenyl)-8-methylchroman-7-ol, (3R,4S)-3-(4-hydroxy-3,5-dimethoxyphenyl)-4-(4-hydroxyphenyl)-8-methylchroman-7-ol, (3S,4R)-3-(4-hydroxy-3,5-dimethoxyphenyl)-4-(4-hydroxyphenyl)-8-methylchroman-7-ol, or a salt or solvate thereof.

In certain embodiments, the compound is (3R,4R)-3-(4-hydroxy-3,5-dimethoxyphenyl)-4-(4-hydroxyphenyl)-8-methylchroman-7-ol, or a salt or solvate thereof, which is in a composition that is free, or essentially free, of each one selected from the group consisting of (3S,4S)-3-(4-hydroxy-3,5-dimethoxyphenyl)-4-(4-hydroxyphenyl)-8-methylchroman-7-ol, (3R,4S)-3-(4-hydroxy-3,5-dimethoxyphenyl)-4-

(4-hydroxyphenyl)-8-methylchroman-7-ol, (3S,4R)-3-(4-hydroxy-3,5-dimethoxyphenyl)-4-(4-hydroxyphenyl)-8-methylchroman-7-ol, or a salt or solvate thereof.

The compounds of the invention may possess one or more stereocenters, and each stereocenter may exist independently in either the (R) or (S) configuration. In certain embodiments, compounds described herein are present in optically active or racemic forms. The compounds described herein encompass racemic, optically active, regioisomeric and stereoisomeric forms, or combinations thereof that possess the therapeutically useful properties described herein. Preparation of optically active forms is achieved in any suitable manner, including by way of non-limiting example, by resolution of the racemic form with recrystallization techniques, synthesis from optically active starting materials, chiral synthesis, or chromatographic separation using a chiral stationary phase. A compound illustrated herein by the racemic formula further represents either of the two enantiomers or mixtures thereof, or in the case where two or more chiral center are present, all diastereomers or mixtures thereof.

In certain embodiments, the compounds of the invention exist as tautomers. All tautomers are included within the scope of the compounds recited herein.

Compounds described herein also include isotopically labeled compounds wherein one or more atoms is replaced by an atom having the same atomic number, but an atomic mass or mass number different from the atomic mass or mass number usually found in nature. Examples of isotopes suitable for inclusion in the compounds described herein include and are not limited to $^{2}H$, $^{3}H$, $^{11}C$, $^{13}C$, $^{14}C$, $^{36}Cl$, $^{18}F$, $^{123}I$, $^{125}I$, $^{13}N$, $^{15}N$, $^{15}O$, $^{17}O$, $^{18}O$, $^{32}P$, and $^{35}S$. In certain embodiments, substitution with heavier isotopes such as deuterium affords greater chemical stability. Isotopically labeled compounds are prepared by any suitable method or by processes using an appropriate isotopically labeled reagent in place of the non-labeled reagent otherwise employed.

In certain embodiments, the compounds described herein are labeled by other means, including, but not limited to, the use of chromophores or fluorescent moieties, bioluminescent labels, or chemiluminescent labels.

In all of the embodiments provided herein, examples of suitable optional substituents are not intended to limit the scope of the claimed invention. The compounds of the invention may contain any of the substituents, or combinations of substituents, provided herein.

The present invention includes pharmaceutical compositions comprising the compound of formula (I). The pharmaceutical compositions described herein may be prepared by any method known or hereafter developed in the art of pharmacology. In general, such preparatory methods include bringing the active ingredient into association with a carrier or one or more other accessory ingredients, and then, if necessary or desirable, shaping or packaging the product into a desired single- or multi-dose unit.

Salts

The compounds described herein may form salts with acids and/or bases, and such salts are included in the present invention. In certain embodiments, the salts are pharmaceutically acceptable salts. The term "salts" embraces addition salts of free acids and/or basis that are useful within the methods of the invention. The term "pharmaceutically acceptable salt" refers to salts that possess toxicity profiles within a range that affords utility in pharmaceutical applications. Pharmaceutically unacceptable salts may nonetheless possess properties such as high crystallinity, which have utility in the practice of the present invention, such as for example utility in process of synthesis, purification or formulation of compounds useful within the methods of the invention.

Suitable pharmaceutically acceptable acid addition salts may be prepared from an inorganic acid or from an organic acid. Examples of inorganic acids include hydrochloric, hydrobromic, hydriodic, nitric, carbonic, sulfuric (including sulfate and hydrogen sulfate), and phosphoric acids (including hydrogen phosphate and dihydrogen phosphate). Appropriate organic acids may be selected from aliphatic, cycloaliphatic, aromatic, araliphatic, heterocyclic, carboxylic and sulfonic classes of organic acids, examples of which include formic, acetic, propionic, succinic, glycolic, gluconic, lactic, malic, tartaric, citric, ascorbic, glucuronic, maleic, malonic, saccharin, fumaric, pyruvic, aspartic, glutamic, benzoic, anthranilic, 4-hydroxybenzoic, phenylacetic, mandelic, embonic (pamoic), methanesulfonic, ethanesulfonic, benzenesulfonic, pantothenic, trifluoromethanesulfonic, 2-hydroxyethanesulfonic, p-toluenesulfonic, sulfanilic, cyclohexylaminosulfonic, stearic, alginic, β-hydroxybutyric, salicylic, galactaric and galacturonic acid.

Suitable pharmaceutically acceptable base addition salts of compounds of the invention include, for example, metallic salts including alkali metal, alkaline earth metal and transition metal salts such as, for example, calcium, magnesium, potassium, sodium and zinc salts. Pharmaceutically acceptable base addition salts also include organic salts made from basic amines such as, for example, N,N'-dibenzylethylene-diamine, chloroprocaine, choline, diethanolamine, ethylenediamine, meglumine (also known as N-methylglucamine) and procaine. All of these salts may be prepared from the corresponding compound by reacting, for example, the appropriate acid or base with the compound.

Combination Therapies

In certain embodiments, the compounds of the invention are useful in the methods of present invention when used concurrently with at least one additional compound useful for treating epithelial cancer.

In a non-limiting example, the compounds of the invention are used concurrently or in combination with at least one AMPK activator, chemotherapeutic drug, or salts, solvates, enantiomers, diastereoisomers, or tautomers thereof.

In certain embodiments, the at least one chemotherapeutic drug is at least one selected from the group consisting of Paclitaxel, Cisplatin, Carboplatin, Topotican and Doxoribicin.

In certain embodiments, the at least one AMPK activator is selected from the group consisting of 5-Aminoimidazole-4-carboxamide-1-β-D-ribofuranoside (AICAR), metformin and 5-[3-[4-[2-(4-fluorophenyl)ethoxy]phenyl]propyl]-2-furancarboxylic acid.

A synergistic effect may be calculated, for example, using suitable methods such as, for example, the Sigmoid-$E_{max}$ equation (Holford & Scheiner, 1981, Clin. Pharmacokinet. 6:429-453), the equation of Loewe additivity (Loewe & Muischnek, 1926, Arch. Exp. Pathol Pharmacol. 114: 313-326) and the median-effect equation (Chou & Talalay, 1984, Adv. Enzyme Regul. 22:27-55). Each equation referred to elsewhere herein may be applied to experimental data to generate a corresponding graph to aid in assessing the effects of the drug combination. The corresponding graphs associated with the equations referred to elsewhere herein are the concentration-effect curve, isobologram curve and combination index curve, respectively.

Methods

The present invention includes methods of treating epithelial cancer in a subject in need thereof. The method comprises administering to the subject a therapeutically effective amount of an eutomeric isomer of the compound of formula (I), or a salt or solvate thereof.

In certain embodiments, the compound is part of a pharmaceutical composition or formulation further comprising at least a pharmaceutically acceptable carrier. In other embodiments, the composition further comprises a nanoparticle, wherein the nanoparticle is optionally coated with a peptide comprising ArgGlyAsp. In yet other embodiments, the peptide consists essentially of ArgGlyAsp. In yet other embodiments, the peptide consists of ArgGlyAsp.

In certain embodiments, the compound decreases, and/or prevents or minimizes growth of, the epithelial cancer size. In other embodiments, the compound stops, prevents, hampers and/or minimizes the epithelial cancer growth. In yet other embodiments, the compound stops, prevents, hampers and/or minimizes epithelial cancer metastasis. In yet other embodiments, the compound stops, prevents, delays and/or hampers epithelial cancer recurrence.

In certain embodiments, the epithelial cancer is at least one cancer selected from the group consisting of ovarian, endometrial, pancreatic, renal and colon.

In certain embodiments, the epithelial cancer is ovarian epithelial cancer.

In certain embodiments, the subject is further administered one or more additional agents useful for treating epithelial cancer. In other embodiments, the one or more additional agents are selected from the group consisting of Paclitaxel, Cisplatin, Carboplatin, Topotican and Doxoribicin. In yet other embodiments, the one or more additional agents are selected from the group consisting of 5-Aminoimidazole-4-carboxamide-1-β-D-ribofuranoside (AICAR), metformin and 5-[3-[4-[2-(4-fluorophenyl)ethoxy]phenyl]propyl]-2-furancarboxylic acid. In yet other embodiments, the compound and the one or more additional agents are co-administered to the patient. In yet other embodiments, the compound and the one or more additional agents are coformulated.

In certain embodiments, the compound is administered to the subject by at least one route selected from the group consisting of oral, nasal, inhalational, topical, buccal, rectal, pleural, peritoneal, intra-peritoneal, vaginal, intramuscular, subcutaneous, transdermal, epidural, intratracheal, otic, intraocular, intrathecal, and intravenous routes. In other embodiments, the compound is administered to the subject by intra-peritoneal injection. In yet other embodiments, the compound is administered as part of a nanoparticle composition.

In certain embodiments, the therapeutically effective amount of the compound ranges from about 0.001 mg/day to about 10,000 mg/day. In other embodiments, the therapeutically effective amount of the compound ranges from about 1 mg/kg of body weight/day to about 1,000 mg/kg of body weight/day. In yet other embodiments, the therapeutically effective amount of the compound is about 50, 100 or 150 mg/kg/day.

In certain embodiments, the compound is administered every day. In other embodiments, the compound is administered six days per week with one rest (no-administration) day. In yet other embodiments, the compound is administered five days per week with two rest days. In yet other embodiments, the compound is administered once a day four days per week with three rest days. In yet other embodiments, the compound is administered once a day three days per week with four rest days. The administration days may be consecutive or alternated with one or more rest days.

In certain embodiments, the subject is a mammal. In other embodiments, the subject is human.

Administration/Dosage/Formulations

The regimen of administration may affect what constitutes an effective amount. The therapeutic formulations may be administered to the subject either prior to or after the onset of a disease or disorder contemplated in the invention. Further, several divided dosages, as well as staggered dosages may be administered daily or sequentially, or the dose may be continuously infused, or may be a bolus injection. Further, the dosages of the therapeutic formulations may be proportionally increased or decreased as indicated by the exigencies of the therapeutic or prophylactic situation.

Administration of the compositions of the present invention to a patient, preferably a mammal, more preferably a human, may be carried out using known procedures, at dosages and for periods of time effective to treat a disease or disorder contemplated in the invention. An effective amount of the therapeutic compound necessary to achieve a therapeutic effect may vary according to factors such as the state of the disease or disorder in the patient; the age, sex, and weight of the patient; and the ability of the therapeutic compound to treat a disease or disorder contemplated in the invention. Dosage regimens may be adjusted to provide the optimum therapeutic response. For example, several divided doses may be administered daily or the dose may be proportionally reduced as indicated by the exigencies of the therapeutic situation. A non-limiting example of an effective dose range for a therapeutic compound of the invention is from about 1 and 5,000 mg/kg of body weight/day. The pharmaceutical compositions useful for practicing the invention may be administered to deliver a dose of from 1 ng/kg/day and 100 mg/kg/day. In other embodiments, the therapeutically effective amount of the compound of formula (I) ranges from about 10 µg/kg/day to about 1,000 mg/kg/day. In yet other embodiments, the therapeutically effective amount of the compound of formula (I) is about 100 mg/kg/day.

One of ordinary skill in the art would be able to study the relevant factors and make the determination regarding the effective amount of the therapeutic compound without undue experimentation.

Actual dosage levels of the active ingredients in the pharmaceutical compositions of this invention may be varied so as to obtain an amount of the active ingredient that is effective to achieve the desired therapeutic response for a particular patient, composition, and mode of administration, without being toxic to the patient.

In particular, the selected dosage level depends upon a variety of factors including the activity of the particular compound employed, the time of administration, the rate of excretion of the compound, the duration of the treatment, other drugs, compounds or materials used in combination with the compound, the age, sex, weight, condition, general health and prior medical history of the patient being treated, and like factors well known in the medical arts.

A medical doctor, e.g., physician or veterinarian, having ordinary skill in the art may readily determine and prescribe the effective amount of the pharmaceutical composition required. For example, the physician or veterinarian could start doses of the compounds of the invention employed in the pharmaceutical composition at levels lower than that required in order to achieve the desired therapeutic effect and gradually increase the dosage until the desired effect is achieved.

In particular embodiments, it is advantageous to formulate the compound in dosage unit form for ease of administration and uniformity of dosage. Dosage unit form as used herein refers to physically discrete units suited as unitary dosages for the patients to be treated; each unit containing a predetermined quantity of therapeutic compound calculated to produce the desired therapeutic effect in association with the required pharmaceutical vehicle. The dosage unit forms of the invention are dictated by and directly dependent on (a) the unique characteristics of the therapeutic compound and the particular therapeutic effect to be achieved, and (b) the limitations inherent in the art of compounding/formulating such a therapeutic compound for the treatment of a disease or disorder contemplated in the invention.

In certain embodiments, the compositions of the invention are formulated using one or more pharmaceutically acceptable excipients or carriers. In other embodiments, the pharmaceutical compositions of the invention comprise a therapeutically effective amount of a compound of the invention and a pharmaceutically acceptable carrier. In yet other embodiments, the compound of the invention is the only biologically active agent (i.e., capable of treating cancer, specifically epthelial cancer) in the composition. In yet other embodiments, the compound of the invention is the only biologically active agent (i.e., capable of treating cancer, specifically epithelial cancer) in therapeutically effective amounts in the composition.

The carrier may be a solvent or dispersion medium containing, for example, water, ethanol, polyol (for example, glycerol, propylene glycol, and liquid polyethylene glycol, and the like), suitable mixtures thereof, and vegetable oils. The proper fluidity may be maintained, for example, by the use of a coating such as lecithin, by the maintenance of the required particle size in the case of dispersion and by the use of surfactants. Prevention of the action of microorganisms may be achieved by various antibacterial and antifungal agents, for example, parabens, chlorobutanol, phenol, ascorbic acid, thimerosal, and the like. In many cases, it is preferable to include isotonic agents, for example, sugars, sodium chloride, or polyalcohols such as mannitol and sorbitol, in the composition. Prolonged absorption of the injectable compositions may be brought about by including in the composition an agent which delays absorption, for example, aluminum monostearate or gelatin.

In certain embodiments, the compositions of the invention are administered to the patient in dosages that range from one to five times per day or more. In other embodiments, the compositions of the invention are administered to the patient in range of dosages that include, but are not limited to, once every day, every two days, every three days to once a week, and once every two weeks. It is readily apparent to one skilled in the art that the frequency of administration of the various combination compositions of the invention varies from individual to individual depending on many factors including, but not limited to, age, disease or disorder to be treated, gender, overall health, and other factors. Thus, the invention should not be construed to be limited to any particular dosage regime and the precise dosage and composition to be administered to any patient is determined by the attending physical taking all other factors about the patient into account.

In certain embodiments, the compositions of the invention are administered after a standard course of chemotherapy has been completed. In other embodiments the compositions of the invention are administered as a maintenance treatment. In certain embodiments, the maintenance treatments of the compound of formula (I) ranges from about 10 mg/kg/day to about 1,000 mg/kg/day. In yet other embodiments, the therapeutically effective amount of the compound of formula (I) is about 50-150 mg/kg/day. In yet other embodiments, the therapeutically effective amount of the compound of formula (I) is about 100 mg/kg/day. In yet other embodiments, the maintenance treatments are administered once per day and every day. In yet other embodiments, the maintenance treatments are administered once a day, six days per week with one rest day therein. In yet other embodiments, the maintenance treatments are administered once a day, five days per week with two rest days. In yet other embodiments, the maintenance treatments are administered once a day, four days per week with three rest days. In yet other embodiments, the maintenance treatments are administered once a day, three days per week with four rest days. The administration days may be consecutive or alternated with one or more rest days.

Compounds of the invention for administration may be in the range of from about 1 µg to about 10,000 mg, about 20 µg to about 9,500 mg, about 40 µg to about 9,000 mg, about 75 µg to about 8,500 mg, about 150 µg to about 7,500 mg, about 200 µg to about 7,000 mg, about 3050 µg to about 6,000 mg, about 500 µg to about 5,000 mg, about 750 µg to about 4,000 mg, about 1 mg to about 3,000 mg, about 10 mg to about 2,500 mg, about 20 mg to about 2,000 mg, about 25 mg to about 1,500 mg, about 30 mg to about 1,000 mg, about 40 mg to about 900 mg, about 50 mg to about 800 mg, about 60 mg to about 750 mg, about 70 mg to about 600 mg, about 80 mg to about 500 mg, and any and all whole or partial increments there between.

In some embodiments, the dose of a compound of the invention is from about 1 mg and about 2,500 mg. In some embodiments, a dose of a compound of the invention used in compositions described herein is less than about 10,000 mg, or less than about 8,000 mg, or less than about 6,000 mg, or less than about 5,000 mg, or less than about 3,000 mg, or less than about 2,000 mg, or less than about 1,000 mg, or less than about 500 mg, or less than about 200 mg, or less than about 50 mg. Similarly, in some embodiments, a dose of a second compound as described herein is less than about 1,000 mg, or less than about 800 mg, or less than about 600 mg, or less than about 500 mg, or less than about 400 mg, or less than about 300 mg, or less than about 200 mg, or less than about 100 mg, or less than about 50 mg, or less than about 40 mg, or less than about 30 mg, or less than about 25 mg, or less than about 20 mg, or less than about 15 mg, or less than about 10 mg, or less than about 5 mg, or less than about 2 mg, or less than about 1 mg, or less than about 0.5 mg, and any and all whole or partial increments thereof.

In certain embodiments, the present invention is directed to a packaged pharmaceutical composition comprising a container holding a therapeutically effective amount of a compound of the invention, alone or in combination with a second pharmaceutical agent; and instructions for using the compound to treat, prevent, or reduce one or more symptoms of a disease or disorder contemplated in the invention.

Formulations may be employed in admixtures with conventional excipients, i.e., pharmaceutically acceptable organic or inorganic carrier substances suitable for intraperitoneal, oral, parenteral, nasal, intravenous, subcutaneous, enteral, or any other suitable mode of administration, known to the art. The pharmaceutical preparations may be sterilized and if desired mixed with auxiliary agents, e.g., lubricants, preservatives, stabilizers, wetting agents, emulsifiers, salts for influencing osmotic pressure buffers, coloring, flavoring and/or aromatic substances and the like. They may also be combined where desired with other active agents.

Routes of administration of any of the compositions of the invention include intra-peritoneal, oral, nasal, rectal, intravaginal, parenteral, buccal, sublingual or topical. The compounds for use in the invention may be formulated for administration by any suitable route, such as for oral or parenteral, for example, transdermal, transmucosal (e.g., sublingual, lingual, (trans)buccal, (trans)urethral, vaginal (e.g., trans- and perivaginally), (intra)nasal and (trans)rectal), intravesical, intrapulmonary, intraduodenal, intragastrical, intrathecal, subcutaneous, intramuscular, intradermal, intra-peritoneal, intra-arterial, intravenous, intrabronchial, inhalation, and topical administration.

Suitable compositions and dosage forms include, for example, tablets, capsules, caplets, pills, gel caps, troches, dispersions, suspensions, solutions, syrups, granules, beads, transdermal patches, gels, powders, pellets, magmas, lozenges, creams, pastes, plasters, lotions, discs, suppositories, liquid sprays for nasal or oral administration, dry powder or aerosolized formulations for inhalation, compositions and formulations for intravesical administration and the like. It should be understood that the formulations and compositions that would be useful in the present invention are not limited to the particular formulations and compositions that are described herein.

Parenteral Administration

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intravenous, intraperitoneal, intramuscular, intrasternal injection, and kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules or in multidose containers containing a preservative. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e., powder or granular) form for reconstitution with a suitable vehicle (e.g., sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butanediol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer system. Compositions for sustained release or implantation may comprise pharmaceutically acceptable polymeric or hydrophobic materials such as an emulsion, an ion exchange resin, a sparingly soluble polymer, or a sparingly soluble salt.

Controlled Release Formulations and Drug Delivery Systems

In certain embodiments, the formulations of the present invention may be, but are not limited to, short-term, rapid-offset, as well as controlled, for example, sustained release, delayed release and pulsatile release formulations.

The term sustained release is used in its conventional sense to refer to a drug formulation that provides for gradual release of a drug over an extended period of time, and that may, although not necessarily, result in substantially constant blood levels of a drug over an extended time period. The period of time may be as long as a month or more and should be a release which is longer that the same amount of agent administered in bolus form.

For sustained release, the compounds may be formulated with a suitable polymer or hydrophobic material that provides sustained release properties to the compounds. As such, the compounds useful within the methods of the invention may be administered in the form of microparticles, for example by injection, or in the form of wafers or discs by implantation.

In one embodiment of the invention, the compounds of the invention are administered to a patient, alone or in combination with another pharmaceutical agent, using a sustained release formulation.

The term delayed release is used herein in its conventional sense to refer to a drug formulation that provides for an initial release of the drug after some delay following drug administration and that may, although not necessarily, includes a delay of from about 10 minutes up to about 12 hours.

The term pulsatile release is used herein in its conventional sense to refer to a drug formulation that provides release of the drug in such a way as to produce pulsed plasma profiles of the drug after drug administration.

The term immediate release is used in its conventional sense to refer to a drug formulation that provides for release of the drug immediately after drug administration.

As used herein, short-term refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any or all whole or partial increments thereof after drug administration after drug administration.

As used herein, rapid-offset refers to any period of time up to and including about 8 hours, about 7 hours, about 6 hours, about 5 hours, about 4 hours, about 3 hours, about 2 hours, about 1 hour, about 40 minutes, about 20 minutes, about 10 minutes, or about 1 minute and any and all whole or partial increments thereof after drug administration.

Dosing

The therapeutically effective amount or dose of a compound of the present invention depends on the age and weight of the patient, the current medical condition of the patient and the progression of a disease or disorder contemplated in the invention. The skilled artisan is able to determine appropriate dosages depending on these and other factors.

A suitable dose of a compound of the present invention may be in the range of from about 0.01 mg to about 5,000 mg per day, such as from about 0.1 mg to about 1,000 mg, for example, from about 1 mg to about 500 mg, such as about 5 mg to about 250 mg per day. The dose may be administered in a single dosage or in multiple dosages, for example from 1 to 5 or more times per day. When multiple dosages are used, the amount of each dosage may be the same or different. For example, a dose of 1 mg per day may be administered as two 0.5 mg doses, with about a 12-hour interval between doses.

It is understood that the amount of compound dosed per day may be administered, in non-limiting examples, every day, every other day, every 2 days, every 3 days, every 4 days, or every 5 days. For example, with every other day administration, a 5 mg per day dose may be initiated on Monday with a first subsequent 5 mg per day dose administered on Wednesday, a second subsequent 5 mg per day dose administered on Friday, and so on.

In the case wherein the patient's status does improve, upon the doctor's discretion the administration of the inhibitor of the invention is optionally given continuously; alternatively, the dose of drug being administered is temporarily reduced or temporarily suspended for a certain length of time (i.e., a "drug holiday"). The length of the drug holiday optionally varies between 2 days and 1 year, including by way of example only, 2 days, 3 days, 4 days, 5 days, 6 days, 7 days, 10 days, 12 days, 15 days, 20 days, 28 days, 35 days, 50 days, 70 days, 100 days, 120 days, 150 days, 180 days, 200 days, 250 days, 280 days, 300 days, 320 days, 350 days, or 365 days. The dose reduction during a drug holiday includes from 10%-100%, including, by way of example only, 10%, 15%, 20%, 25%, 30%, 35%, 40%, 45%, 50%, 55%, 60%, 65%, 70%, 75%, 80%, 85%, 90%, 95%, or 100%.

Once improvement of the patient's conditions has occurred, a maintenance dose is administered if necessary. Subsequently, the dosage or the frequency of administration, or both, is reduced, as a function of the disease or disorder, to a level at which the improved disease is retained. In certain embodiments, patients require intermittent treatment on a long-term basis upon any recurrence of symptoms and/or infection.

The compounds for use in the method of the invention may be formulated in unit dosage form. The term "unit dosage form" refers to physically discrete units suitable as unitary dosage for patients undergoing treatment, with each unit containing a predetermined quantity of active material calculated to produce the desired therapeutic effect, optionally in association with a suitable pharmaceutical carrier. The unit dosage form may be for a single daily dose or one of multiple daily doses (e.g., about 1 to 5 or more times per day). When multiple daily doses are used, the unit dosage form may be the same or different for each dose.

Toxicity and therapeutic efficacy of such therapeutic regimens are optionally determined in cell cultures or experimental animals, including, but not limited to, the determination of the $LD_{50}$ (the dose lethal to 50% of the population) and the $ED_{50}$ (the dose therapeutically effective in 50% of the population). The dose ratio between the toxic and therapeutic effects is the therapeutic index, which is expressed as the ratio between $LD_{50}$ and $ED_{50}$. The data obtained from cell culture assays and animal studies are optionally used in formulating a range of dosage for use in human. The dosage of such compounds lies preferably within a range of circulating concentrations that include the $ED_{50}$ with minimal toxicity. The dosage optionally varies within this range depending upon the dosage form employed and the route of administration utilized.

Those skilled in the art will recognize, or be able to ascertain using no more than routine experimentation, numerous equivalents to the specific procedures, embodiments, claims, and examples described herein. Such equivalents were considered to be within the scope of this invention and covered by the claims appended hereto. For example, it should be understood that modifications in reaction conditions, including but not limited to reaction times or size/volume, and experimental reagents, such as solvents, catalysts, pressures, atmospheric conditions, e.g., nitrogen atmosphere, and reducing/oxidizing agents, with art-recognized alternatives and using no more than routine experimentation, are within the scope of the present application.

It is to be understood that, wherever values and ranges are provided herein, the description in range format is merely for convenience and brevity and should not be construed as an inflexible limitation on the scope of the invention. Accordingly, all values and ranges encompassed by these values and ranges are meant to be encompassed within the scope of the present invention. Moreover, all values that fall within these ranges, as well as the upper or lower limits of a range of values, are also contemplated by the present application. The description of a range should be considered to have specifically disclosed all the possible sub-ranges as well as individual numerical values within that range and, when appropriate, partial integers of the numerical values within ranges. For example, description of a range such as from 1 to 6 should be considered to have specifically disclosed sub-ranges such as from 1 to 3, from 1 to 4, from 1 to 5, from 2 to 4, from 2 to 6, from 3 to 6 etc., as well as individual numbers within that range, for example, 1, 2, 2.7, 3, 4, 5, 5.3, and 6. This applies regardless of the breadth of the range.

The following examples further illustrate aspects of the present invention. However, they are in no way a limitation of the teachings or disclosure of the present invention as set forth herein.

EXAMPLES

The invention is now described with reference to the following Examples. These Examples are provided for the purpose of illustration only, and the invention is not limited to these Examples, but rather encompasses all variations that are evident as a result of the teachings provided herein.

Materials and Methods

Cell Cultures and Conditions

CD44+/MyD88+ ovarian cancer stem cell clones (OCSC1 and OCSC2) and CD44−/MyD88− ovarian cancer cells (OCC1 and OCC2) were isolated from either tumor tissue or ascites obtained from patients diagnosed with stage III/IV serous ovarian cancer and propagated (Alvero, et al., 2009, Cell Cycle 8:158-166; Chefetz, et al., 2013, Cell Cycle 12:511-521). The epithelial nature of the isolated cells was determined by immunostaining for Ck18. Purity of the cultures based on CD44 expression by flow cytometry and chemoresistance were routinely tested. Stable expression of nuclear-restricted red fluorescent (in OCSCs) or green fluorescent proteins (in OCCs) was performed by transduction using NUCLIGHT® Red or Green Lentivirus Reagent (Essen Bioscience, Ann Arbor, Mich.). Spheroids were formed from OCSCs by culturing in ultra-low attachment multi-well plates (Corning, Inc., Corning, N.Y.).

Reagents and Treatments

The SBP panel was obtained from Novogen Ltd. (Hornsby Westfield, NSW, Australia). The synthesis of the SBP library was completed using a four-step process comprised of: acylation of a phenolic compound with a benzoic acid under phosphorous oxychloride/zinc chloride conditions; cyclisation using a substituted acetic acid and Heunig's base; a global deprotection and partial reduction using a Borane reagent; and final catalytic reduction using Palladium based catalyst. The racemate was separated into the two enantiomers using chiral SFC conditions with a Chiracel OD-H column and carbon dioxide and methanol as mobile phases. Detailed synthetic information is found in the PCT Patent Application No WO2015117202 and US20160340329, all of which are incorporated herein in their entireties by reference. SP600125 and U0126 were obtained from Tocris (Bio-Techne, Minneapolis, Minn.). Cisplatin and Paclitaxel used for in vitro testing were obtained from Sigma-Aldrich, Corp. (St. Louis, Mo.). For in vivo studies, Cisplatin and Paclitaxel were obtained from Mylan Institutional (Rockford, Ill.) and APP Pharmaceuticals (Schaumburg, Ill.) respectively.

Real-Time Measurement of Cell Number and Cell Death and Calculation of $IC_{50}$ Effect of each compound on cell morphology, growth, and viability was assessed using a kinetic live cell imaging system (Incucyte, Essen Bioscience). Proliferation was calculated as previously described (Alvero, et al., 2011, Mol. Cancer Ther. 10:1385-1393) using metrics from either confluence or fluorescent count from nuclear-restricted RFP or GFP. Cell death was quantified; similarly CELLTOX® Green Cytotoxicity Assay (Promega, Madison, Wis.). $IC_{50}$ was calculated as described using GraphPad Prism (GraphPad Software Inc., LaJolla, Calif.).

Caspase Activity

Total protein was extracted and measured as described in Kamsteeg, et al., 2003, Oncogene 22:2611-2620. Activity of caspase 3/7 and caspase 9 was quantified using Caspase Glo assay (Promega).

Western Blot Analysis

SDS-PAGE and Western blots were performed using 20 µg of total protein lysate as described in Kamsteeg, et al., 2003, Oncogene 22:2611-2620. Antibodies used were: mouse anti-phospho ERK (Santa Cruz Biotechnology, Inc., Dallas, Tex.); rabbit anti-phospho c-Jun, rabbit anti c-Jun, rabbit anti-ERK, rabbit anti-cleaved caspase 3 all from Cell Signaling Technology, Danvers, Mass.; and mouse anti-GAPDH (Sigma-Aldrich).

Mouse Xenograft Studies

The Yale University Institutional Animal Care and Use Committee approved all in vivo studies described. Intraperitoneal tumors were established in athymic nude mice using $4 \times 10^6$ mCherry+OCSC1-F2 ovarian cancer cells (Craveiro, et al., 2013, Cancer Med. 2:751-762). Injection of cancer cells is designated as day 0 and treatment commenced between day 3-5. Establishment of i.p. tumors was confirmed by live imaging (In-Vivo FX PRO, Bruker Corp., Billerica, Mass.) prior to treatment. TRX-E-002-1 was prepared in 20% Captisol or Dexsolve and administered daily at 50 mg/kg or 100 mg/kg. Paclitaxel was given at 12 mg/kg q3d and Cisplatin at 5 mg/kg weekly. All treatments were given i.p. Tumor growth was monitored q3d by live imaging and response to treatment was assessed using ROI area.

Statistical Analysis

Data was graphed and analyzed using GraphPad Prism. Significance was calculated using two-way ANOVA with Dunnett's correction for multiple comparison and p<0.05 is considered significant.

Example 1

Identification of TRX-E-002 as a Potent Inducer of Ovarian Cancer Stem Cell Death A panel of four different SBP subfamilies with cytotoxic activity against chemoresistant ovarian cancer stem cells were tested for efficacy in inducing ovarian cancer stem cell death. The analogs were screened against two clones of chemoresistant OCSCs (OCSC1 and OCSC2), which have demonstrated resistance to various chemotherapeutic drugs and thus represent the therapeutically relevant ovarian cancer cell subtype. The efficacy of each analog was determined based on its $IC_{50}$. Once an analog demonstrated efficacy in the µM range, structural modifications were made using an iterative structure-activity screening methodology, with the goal of increasing potency and achieving an $IC_{50}$ in the nM range. Out of 40 analogs screened, TRX-E-002 was identified, which was cytotoxic against the two clones of chemoresistant OCSCs with $IC_{50}$ values<0.245 µM (FIG. 1A).

Figure 1B:
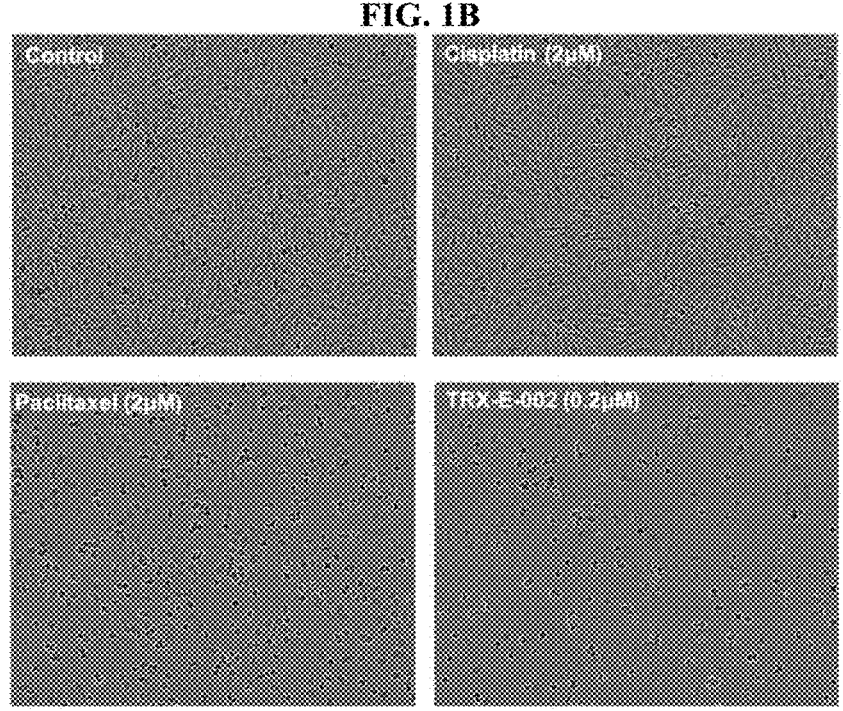

In vitro, conventional chemotherapeutic drugs had negligible effect on OCSC growth even in the µM range (FIG. 1B). In contrast, TRX-E-002 showed a persistent growth inhibitory effect in these low concentrations (FIGS. 1B-1C). Microscopic evaluation of the cultures showed a higher percentage of apoptotic cells in the TRX-E-002 treated cultures compared with those treated with Cisplatin or Paclitaxel (FIG. 1B). These results demonstrate that TRX-E-002 induces a rapid, persistent, and significant anti-tumor activity at low concentrations.

Example 2

TRX-E-002-1 (Enantiomer 1) as the Active Component of TRX-E-002

Figure 1E:
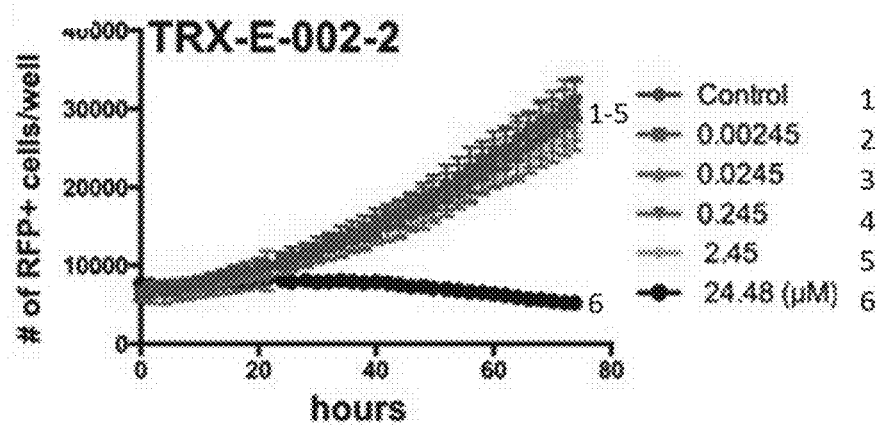
Figure 1F:
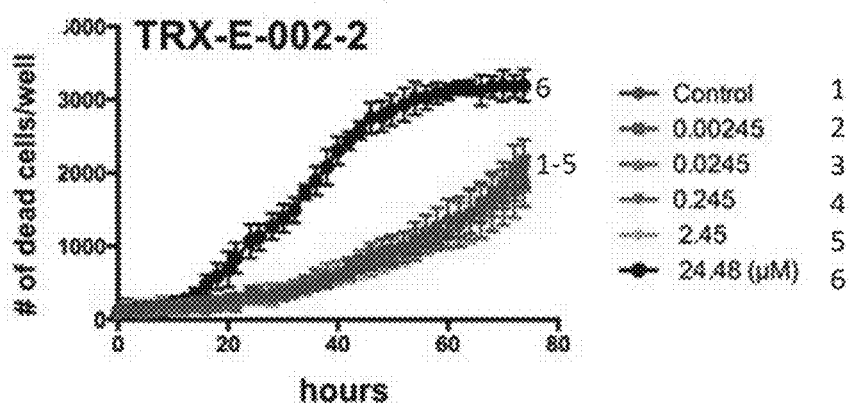
Figure 1F:
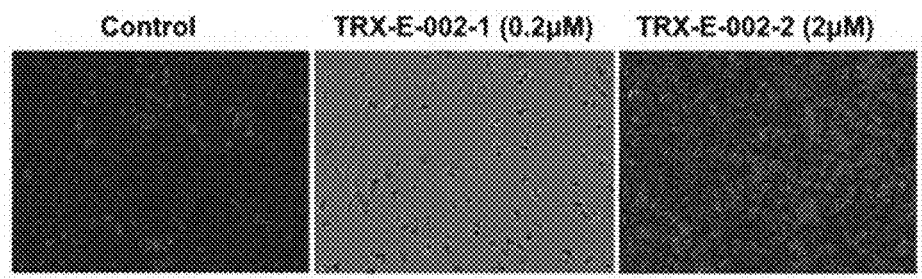
Figure 1G:
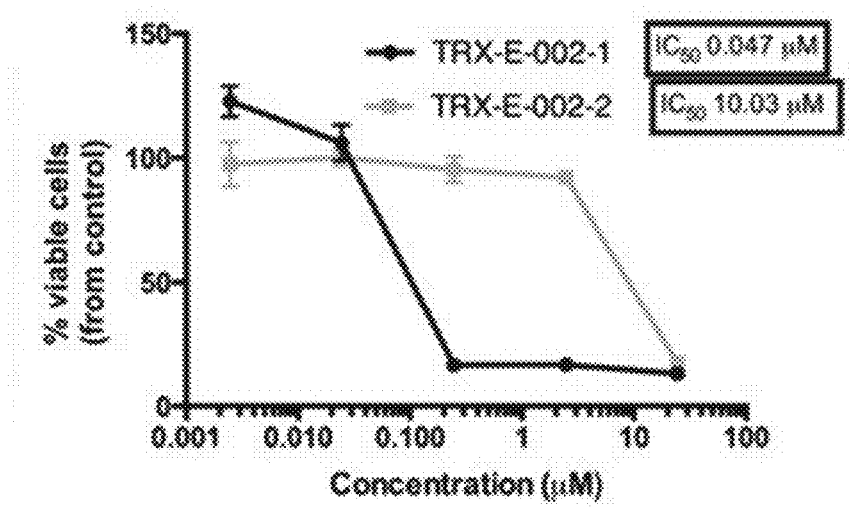

TRX-E-002 exists as a racemic mixture comprised of two enantiomers, enantiomer A (TRX-E-002-1) and enantiomer B (TRX-E-002-2). Thus, the enantiomers were separated and assessed separately. To distinguish between an analog's cytostatic or cytotoxic activity, OCSC clones that are stably transfected with nuclear-restricted RFP were used, which allows an accurate quantification of the number of cells and can be multiplexed with CELLTOX® assay to concomitantly measure the number of dead cells. Evidence of selective enantiomeric activity for enantiomer 1 or TRX-E-002-1 was observed, which elicits a significant decrease in the number of nuclear RFP+ cells (FIG. 1D) and a concomitant increase in the number of Celltox-positive cells (FIG. 1D) beginning at the 0.245 µM dose. In contrast, TRX-E-002-2 was mostly ineffective, except for the very high dose of 10 µM (FIGS. 1D-1E). FIG. 1F shows the morphological changes associated with the effect of these compounds on OCSC2. The $IC_{50}$ for TRX-E-002-1 was 47 nM, while the $IC_{50}$ for TRX-E-002-2 was 10.03 µM (FIG. 1G). Based on these results, TRX-E-002-1 was used as the active pharmaceutical ingredient to further characterize the cytotoxic effect on ovarian cancer cells.

Example 3

TRX-E-002-1 Against Heterogeneous Ovarian Cancer Cells

Figure 2A:
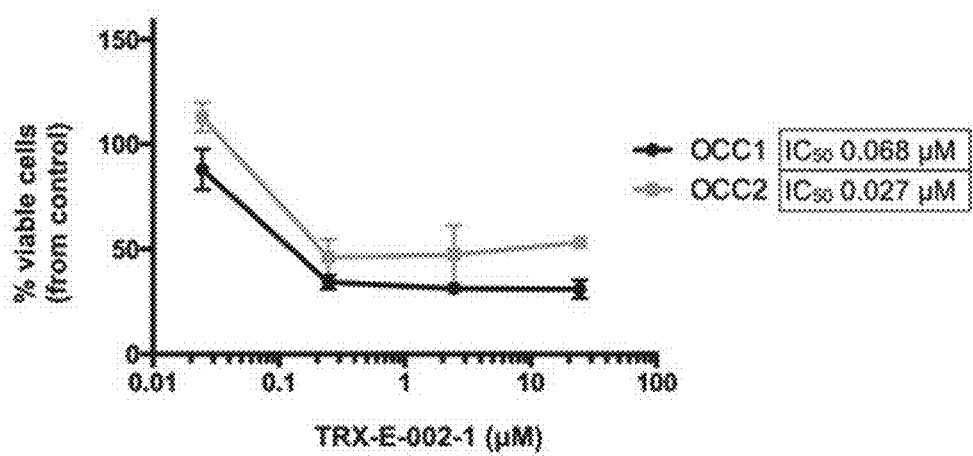

Once the efficacy of TRX-E-002-1 against chemoresistant OCSC was established, its activity against two clones of chemosensitive ovarian cancer cells (OCC1 and OCC2) was determined. The results show that TRX-E-002-1 was effective against both clones and decreased the percentage of viable cells in a dose dependent manner with $IC_{50}$=68 nM and 27 nM for OCC1 and OCC2, respectively (FIG. 2A).

Figure 2B:
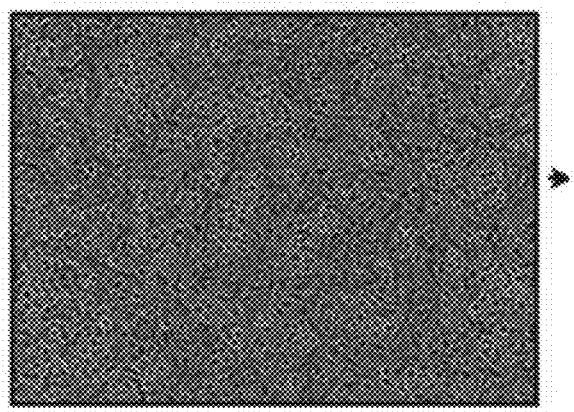
Figure 2B:
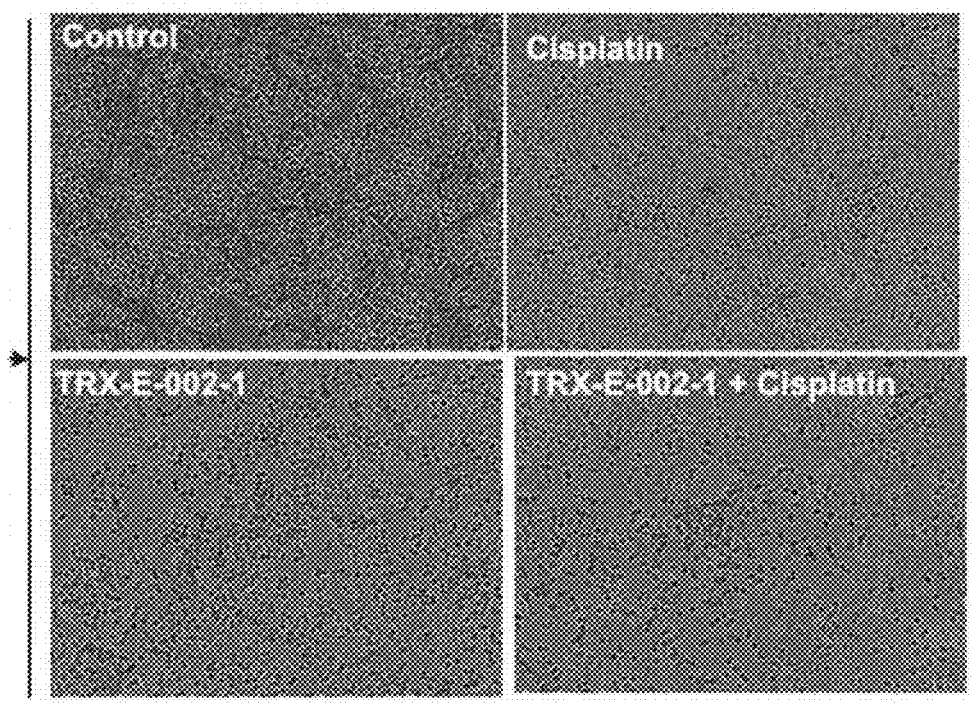
Figure 2C:
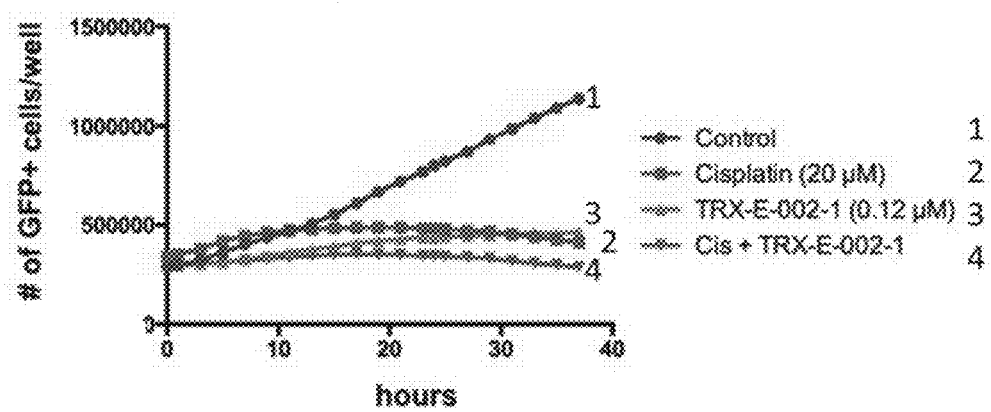
Figure 2C:
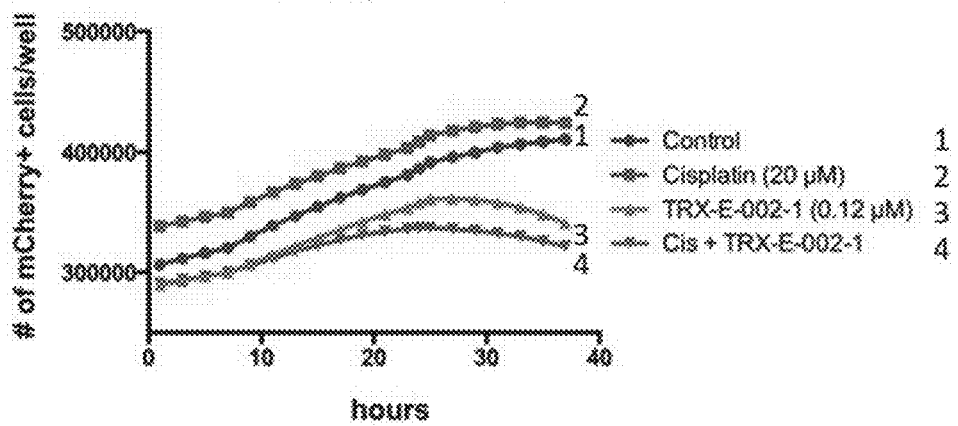

Without wishing to be limited by any theory, response to chemotherapy may be modified by cross-talk among different cancer cell types within the tumor. Thus, to mimic the heterogeneity of ovarian tumors an in vitro co-culture model consisting of RFP-labeled chemoresistant OCSC2 and GFP-labeled chemosensitive OCC2 was used. The co-cultures, which are comprised of 50% RFP-OCSC2 and 50% GFP-OCC2 at time of treatment, were exposed to TRX-E-002-1, cisplatin, or the combination of both. Since GFP-OCC2 has faster doubling time than RFP-OCSC2, it overtook the control co-cultures by the end of the experiment and thus the control co-cultures are mainly comprised of GFP-OCC2 by the 24 h time-point (FIG. 2B). Cisplatin mainly affected GFP-OCC2, as evidenced by a decrease in the number of GFP+ cells (FIGS. 2B-2C), but had no effect on the number of mCherry+ cells (FIGS. 2B-2C), demonstrating a lack of efficacy against the chemoresistant OCSC. Conversely, TRX-E-002-1 markedly reduced the number of both GFP-OCC2 and RFP-OCSC2, indicating that TRX-E-002-1 is highly potent against both ovarian cancer cell subtypes (FIGS. 2B-2C). The addition of Cisplatin to TRX-E-002-1 enhanced the overall cytotoxic effect. These results suggest that the combination TRX-E-002-1 and Cisplatin could be more effective in targeting heterogeneous ovarian cancer tumors.

Example 4

TRX-E-002-1 Induced Death in 3D Ovarian Cancer Spheroids

Spheroids represent a 3D in vitro tumor model of multiple cell layers that mimic tumors in vivo. In ovarian cancer, spheroid cultures not only mimic ovarian solid tumors, but also ovarian cancer cells found in malignant ascites. Spheroid cultures allow one to test the capacity of compounds to diffuse through multiple layers of cells and induce cell death. It further allows one to test the efficacy of treatment against the mesenchymal cancer subtype. Spheroid formation is a function of OCSCs, and this correlates with the acquisition of a mesenchymal phenotype, augmented migratory capacity, and enhanced chemoresistance.

Figure 2E:
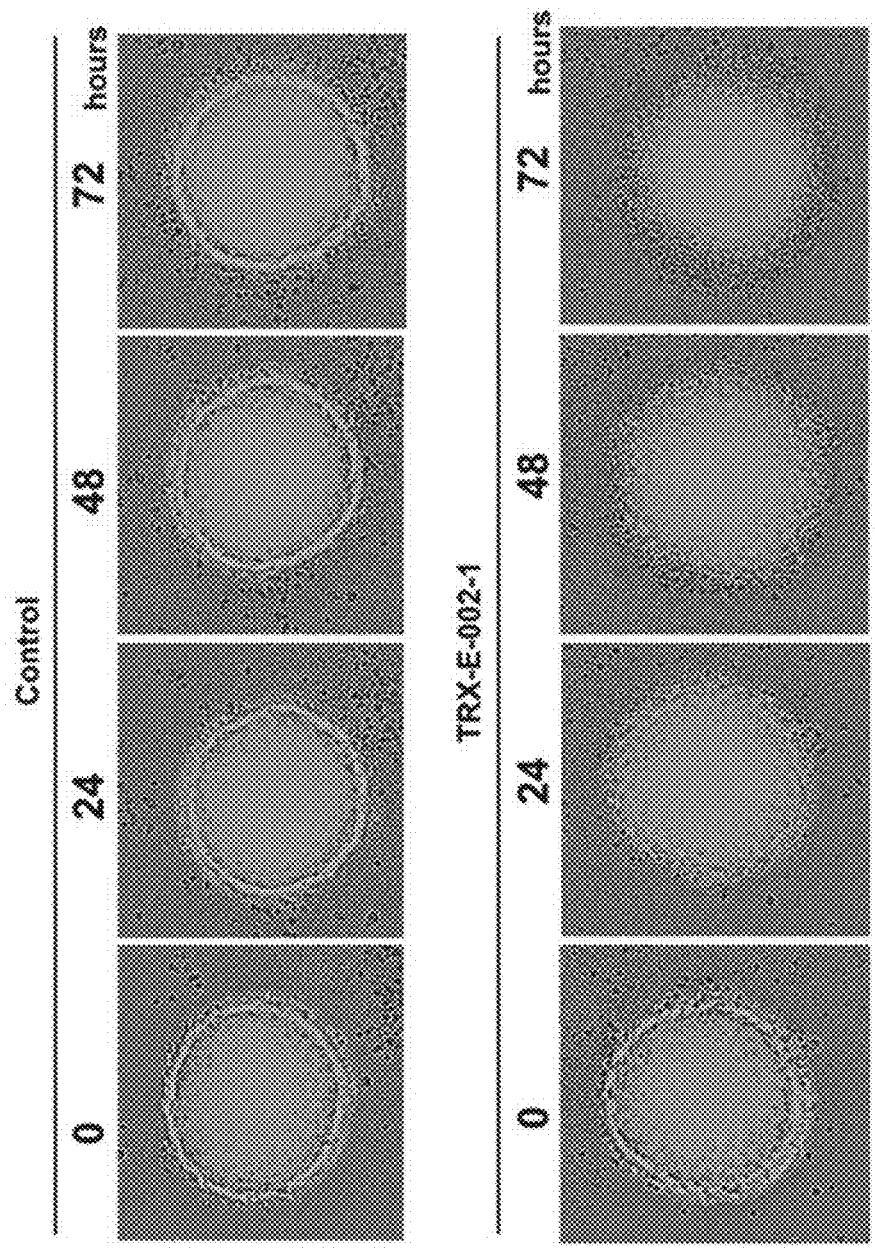

Thus the ability of TRX-E-002-1 to induce cell death in 3D spheroid cultures of OCSC2 was tested by monitoring spheroid integrity using kinetic imaging. Compared to the control, TRX-E-002-1 significantly decreased the amount of intact spheroids in a dose-dependent manner (FIG. 2D) and induced the collapse of their structure (FIG. 2D). This is even more evident when GFP+OCSC2 spheroids were used. While the control spheroids maintained structural integrity through time, TRX-E-002-1 penetrated the multicellular layers of the spheroids and induce cell death in a time-dependent manner (FIG. 2E).

Example 5

TRX-E-002-1 Prevents OCSC Recurrence In Vitro

Figure 3A:
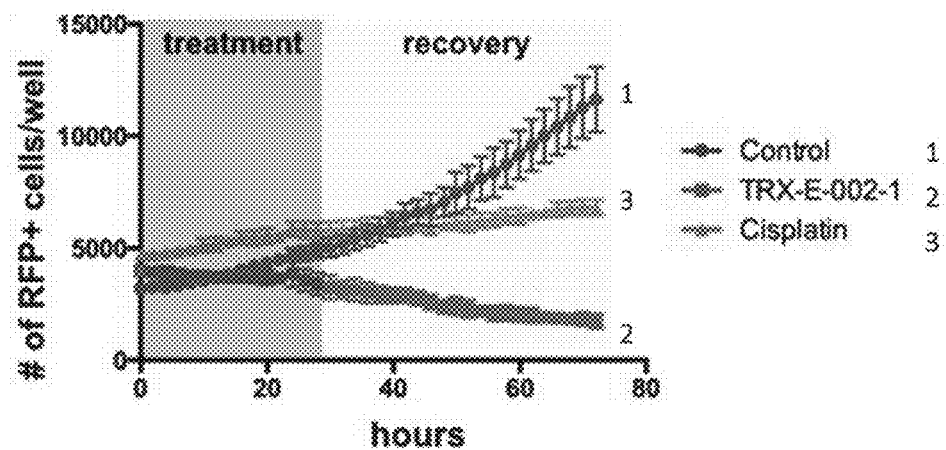
FIGS. 3A-3D demonstrate that TRX-E-002-1 treatment prevents in vitro recovery of ovarian cancer cells.
Figure 3B:
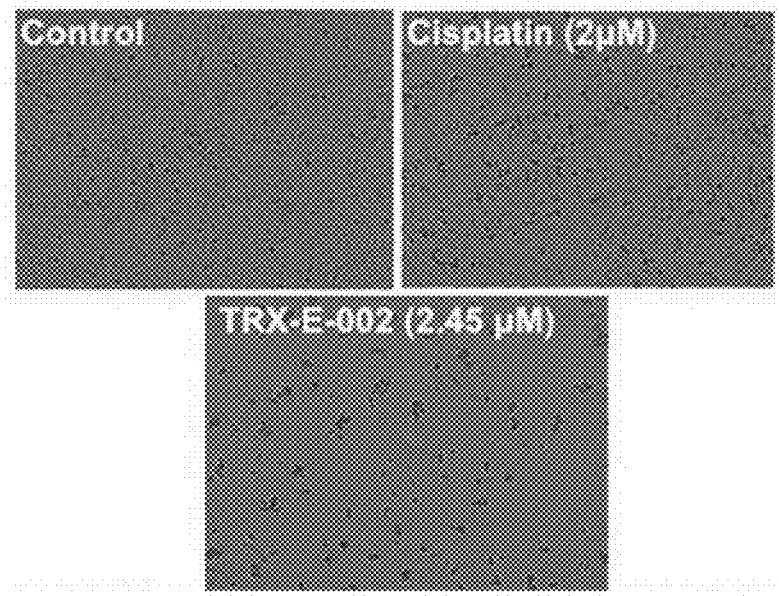

One of the main characteristics of OCSCs is their ability to overcome the cytotoxic effect of chemotherapeutic drugs even after 24 h of treatment in vitro. To determine whether the cytotoxic effect of TRX-E-002-1 is sustained even after its removal, OCSC2 was treated with equivalent doses of TRX-E-002-1 or Cisplatin for 24 h and then removed the treatment, allowing the culture to recover in growth media for another 48 h. In contrast to Cisplatin, TRX-E-002-1 induced a persistent cytotoxic effect on OCSC2 and cells did not recover growth potential after 24 h treatment (FIGS. 3A-3B).

Figure 3C:
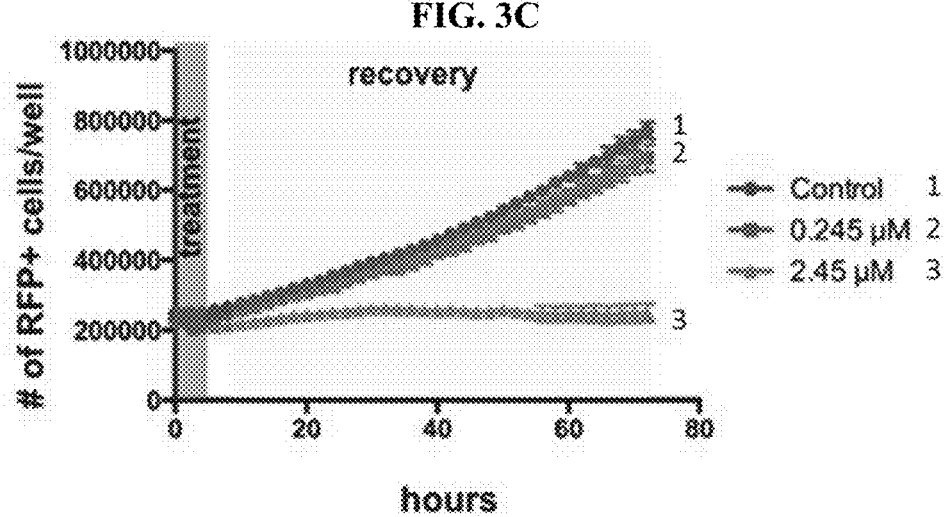
Figure 3D:
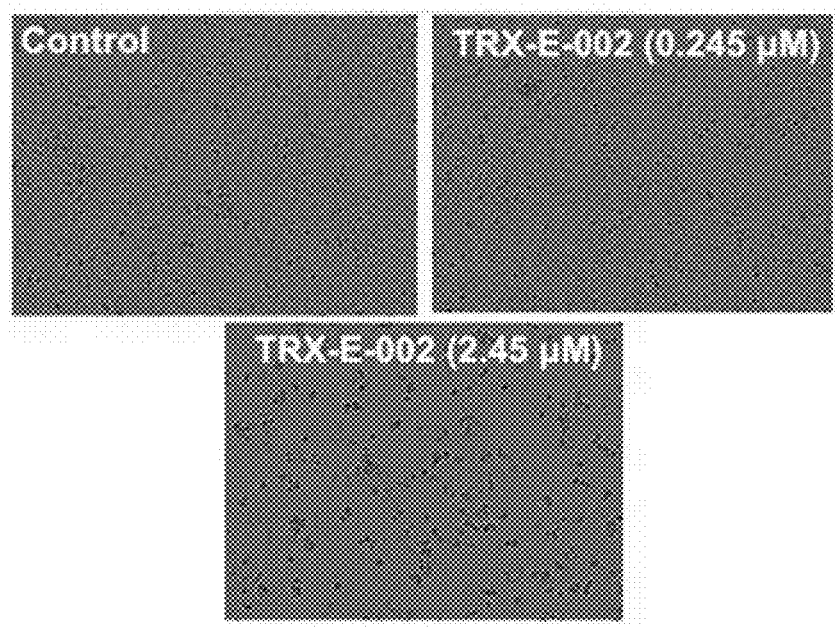

Next, the minimum dose and time necessary for TRX-E-002-1 to confer a sustained cytotoxic effect were evaluated. OCSC cells were exposed to different concentrations of TRX-E-002-1 for 2 h and then allowed to recover in growth media for another 48 h. Two-hour exposure to 2.45 µM of TRX-E-002-1 was sufficient to induce a sustained cytotoxic effect (FIGS. 3C-3D). However, when the concentration of TRX-E-002-1 was decreased to 0.245 µM, 2 h of exposure was not enough, and the cells recovered and resumed proliferative potential (FIGS. 3C-3D). Without wishing to be limited to any theory, molecular changes induced by TRX-E-002-1 during the 2 h exposure with 2.45 µM TRX-E-002-1 can in part help explain its efficacy.

Example 6

TRX-E-002-1-Induced Cell Death is Associated with Phosphorylation and Stabilization of c-Jun In order to elucidate the early pathways responsible for the sustained cytotoxic effect observed with TRX-E-002-1, a phosphokinase array was performed. The phosphokinase array detected relative phosphorylation levels of 43 different kinases involved in major signal transduction pathways.

Figure 4A:
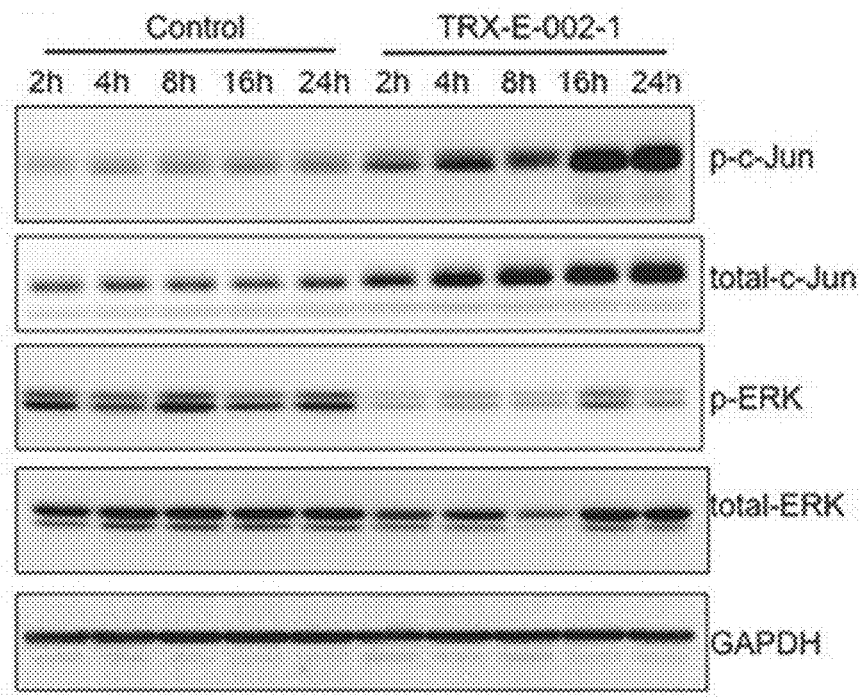
FIGS. 4A-4F depict association between c-Jun phosphorylation and TRX-E-002-1 induced cell death.
Figure 4B:
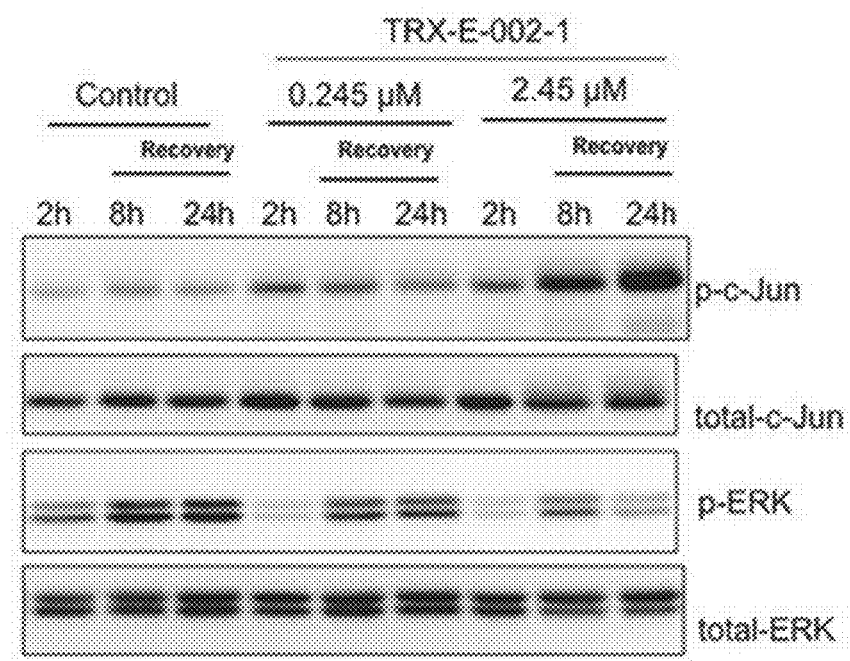

Compared to controls, cells treated with TRX-E-002-1 showed higher levels of phosphorylated c-Jun (p-c-Jun) and lower levels of phosphorylated-ERK (p-ERK). These findings were validated by western blot analysis, which showed a time dependent increase in p-c-Jun accompanied by a time-dependent increase in total c-Jun (FIG. 4A). The western blot results also validated the decrease in p-ERK in cells treated with TRX-E-002-1. At baseline, the cells demonstrated cyclic ERK activation, as evidenced by recurring upregulation and downregulation of p-ERK levels in no treatment controls through time. The effect on the phosphorylation status of the kinases (upregulation of p-cJun and downregulation of p-ERK) was observed as early as 2 h post-treatment and maintained up to 24 h (FIG. 4A). The phosphorylation levels of c-Jun and ERK correlate with the differential ability of the two doses of TRX-E-002-1 to induce a sustained cytotoxic effect. As shown in FIG. 3C, treatment with 2.45 µM TRX-E-002-1 for only 2 h was enough to induce a sustained cytotoxic effect in OCSCs. This correlates with the ability of this dose of TRX-E-002-1 to maintain the upregulation of p-cJun and downregulation of p-ERK even when the compound is removed (FIG. 4B). In contrast, cells treated with of 0.245 µM TRX-E-002-1 recovered proliferative potential (FIG. 3C) and did not sustain the increase in p-c-Jun and the decrease in p-ERK. As such, when the compound was removed after 2 h p-c-Jun and p-ERK returned to levels close to baseline (FIG. 4B). These data show that the sustained upregulation of p-c-Jun and downregulation p-ERK are associated with TRX-E-002-1 induced cell death.

Figure 4C:
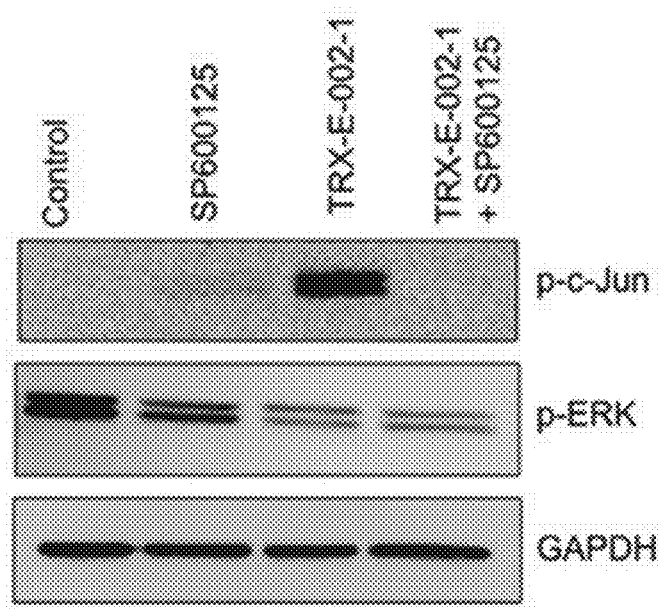
Figure 4D:
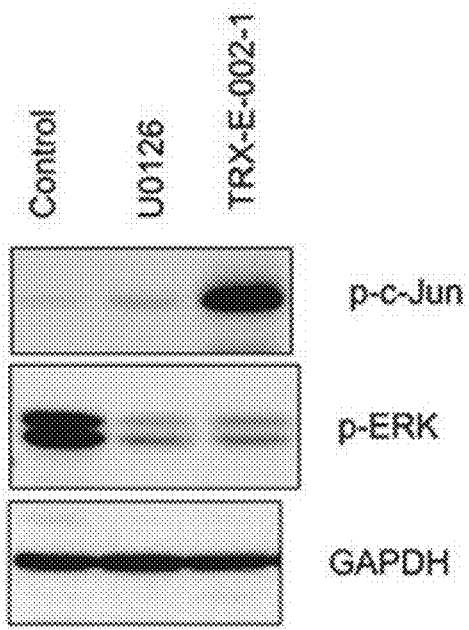
Figure 4E:
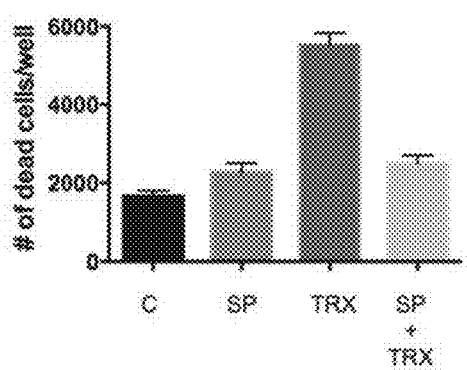

Jun N-terminal kinase (JNK) is a stress-activated protein kinase and the main kinase that phosphorylates c-Jun. To determine whether the JNK/Jun pathway is involved in TRX-E-002-1-induced cell death, the JNK inhibitor SP600125 (1,9-Pyrazoloanthrone; a reversible ATP competitive inhibitor selective for JNK 1, 2, and 3) was used. Cells were treated with TRX-E-002-1 in the presence or absence of SP600125. As shown in FIG. 4C, TRX-E-002-1 induced a significant increase in p-c-Jun and this was abrogated with co-treatment with SP600125. In contrast, SP600125 did not affect the ability of TRX-E-002-1 to downregulate p-ERK suggesting specificity of its activity against the c-Jun pathway (FIG. 4C). Determination of the effect on cell death showed that SP600125 co-treatment rescued OCSCs from TRX-E-002-1-induced cell death (FIG. 4E). These results demonstrate the importance of Jun phosphorylation in TRX-E-002-1-induced cell death.

Figure 4F:
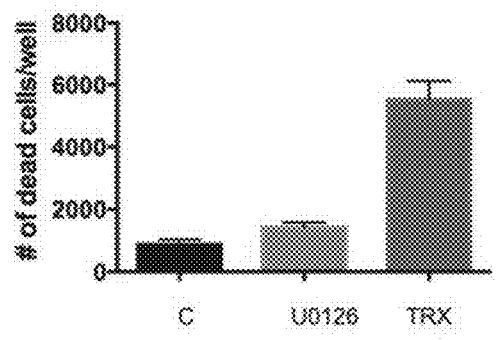

To determine the importance of downregulating the levels of p-ERK, cells were treated with U0126 (1,4-diamino-2,3-dicyano-1,4-bis(2-aminophenylthio)butadiene) to recapitulate the effect of TRX-E-002-1 on the ERK pathway. Western blot analysis showed that U0126 downregulated the levels of p-ERK comparable to levels induced by TRX-E-002-1 (FIG. 4D). However, the effect of U0126 on cell death was not comparable to the effect of TRX-E-002-1 (FIG. 4F), suggesting that inhibition of the ERK pathway may not play a role in the survival of OCSCs and in addition, may not be required for TRX-002-1-induced cell death.

Example 7

TRX-E-002-1 Activates the Apoptotic Cascade

Figure 5A:
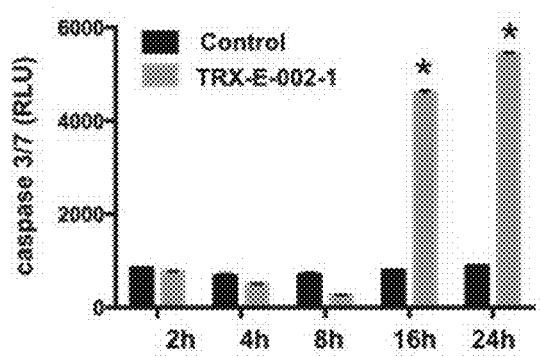
FIGS. 5A-5C illustrate findings that TRX-E-002-1 activates the caspase cascade and requires c-Jun activation.
Figure 5B:
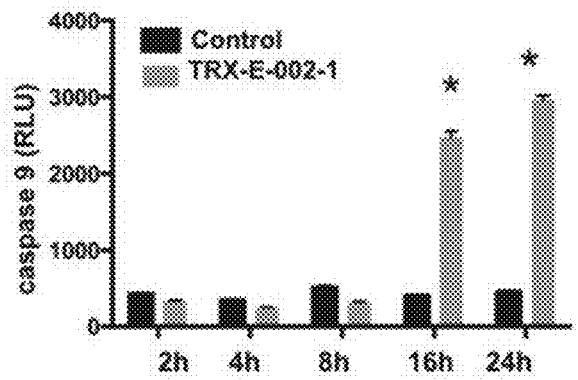

The activities of caspase-3/7 and caspase-9 were assessed at 2, 4, 6, 8, 16, and 24 hours post-treatment with TRX-E-002-1. TRX-E-002-1 induced a significant increase in both caspase-3/7 (FIG. 5A) and caspase-9 (FIG. 5B) activity at 16 and 24 h post treatment. The results demonstrate that TRX-E-002-1 activates the apoptotic cascade in the chemoresistant OCSC cultures.

Figure 5C:
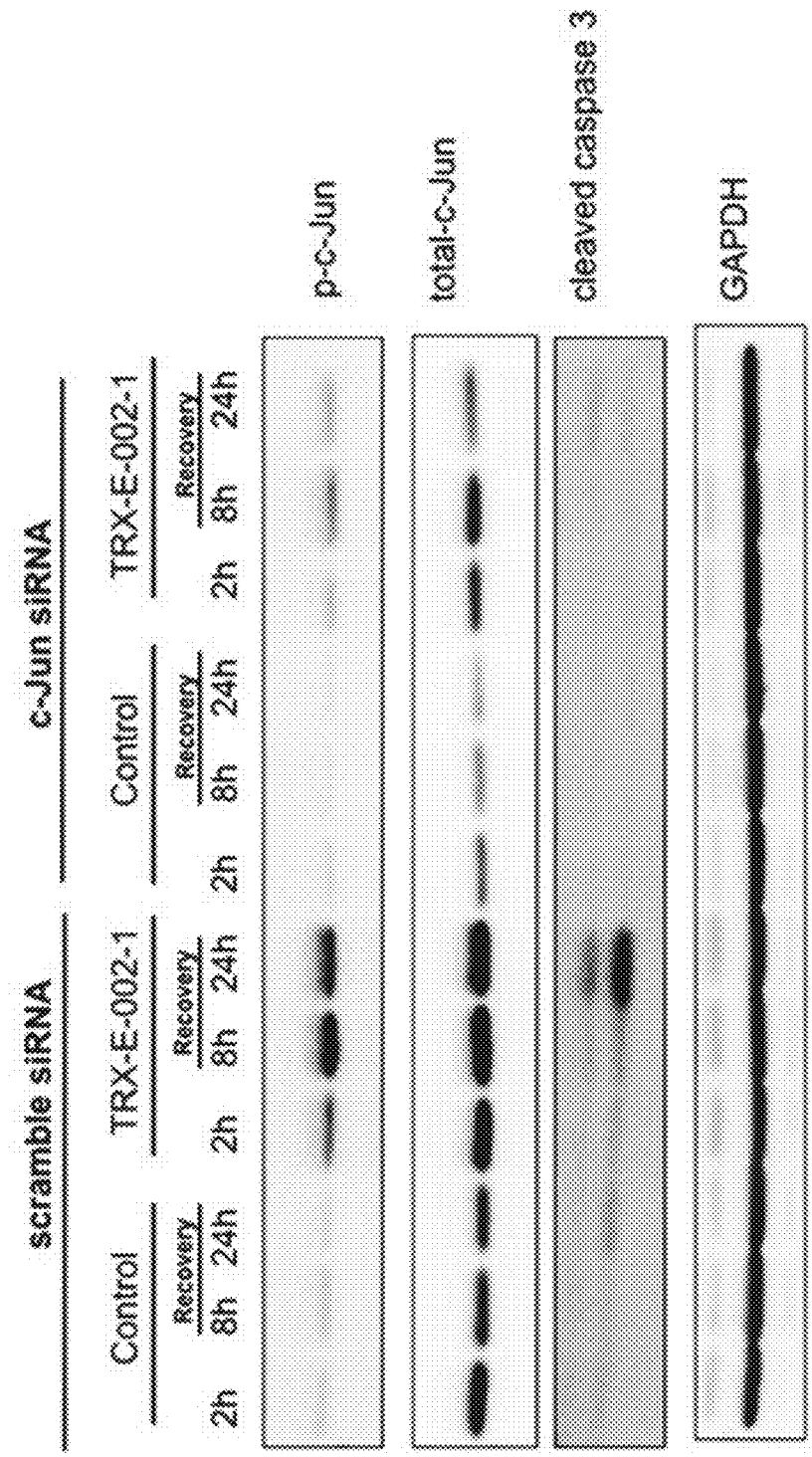

To determine the requirement for c-Jun activation in TRX-E-002-1-induced apoptosis, siRNA was used to knockdown c-Jun in chemoresistant OCSC. In cells transfected with scramble siRNA, similar to results obtained with wt OCSC cells, TRX-E-002-1 upregulated the levels of phospho-c-Jun and total c-Jun within two hours of treatment. This upregulation was maintained, even when treatment was removed and cells were allowed to recover (FIG. 5C). The steady increase in the levels of phospho-c-Jun and total c-Jun in cells treated with TRX-E-002-1 correlates with the appearance of cleaved/active caspase-3. In contrast, in cells wherein c-Jun was knocked-down, although TRX-E-002-1 still upregulated the levels of phospho-c-Jun and total c-Jun compared to no treatment control, these levels are significantly less than observed in cells with scramble siRNA. Consequently, cleaved/active caspase-3 was not detectable.

Example 8

In Vivo Activity of TRX-E-002-1 in an Intra-Peritoneal Ovarian Cancer Xenograft Model An intra-peritoneal (i.p.) recurrent ovarian cancer xenograft model established using ovarian cancer cells stably expressing mCherry fluorescence has been established. This allows the detection of i.p. tumors and real-time measurement of response during the course of treatment. This model recapitulates the clinical profile typically seen in patients with ovarian cancer and helps one answer three questions: (1) in vivo activity of TRX-E-002-1 against primary disease; (2) ability of TRX-E-002-1 given in combination with chemotherapy to prevent/delay recurrence; and (3) ability of TRX-E-002-1 given as maintenance after chemotherapy to prevent/delay recurrence.

Figure 6A:
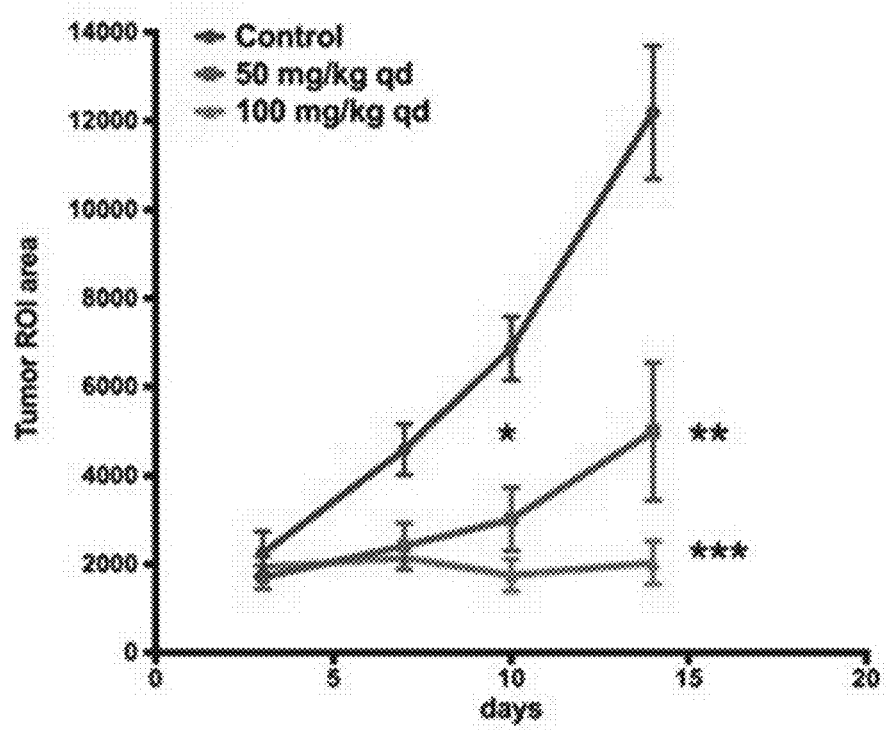
FIGS. 6A-6J illustrate findings that TRX-E-002-1 demonstrates significant anti-tumor activity against both primary and recurrent disease in a mouse xenograft model of ovarian cancer.
Figure 6B:
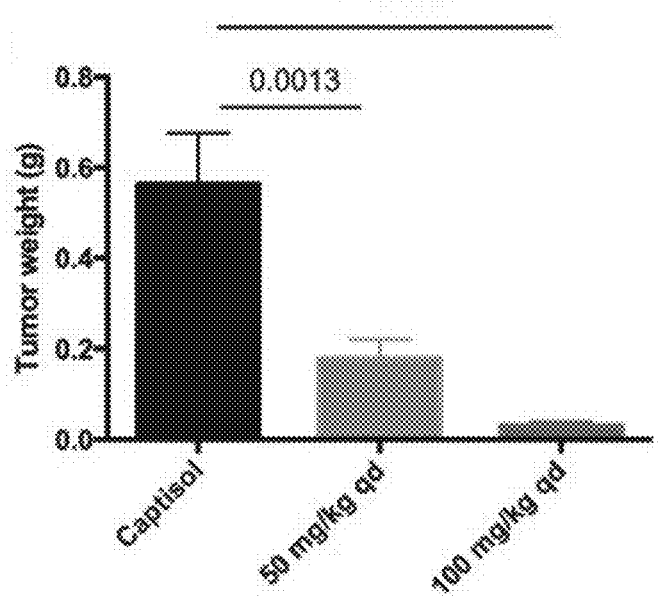
Figure 6C:
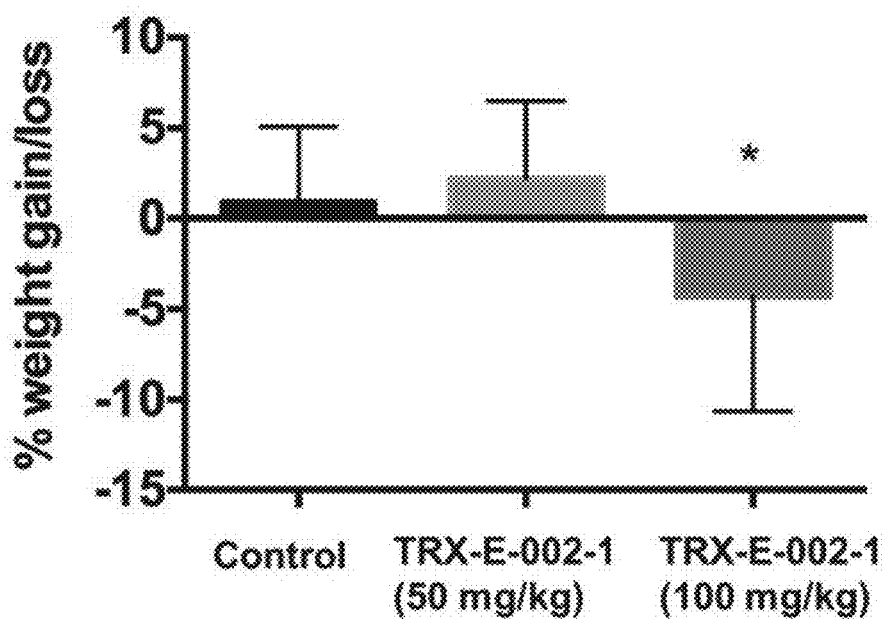
Figure 6D:
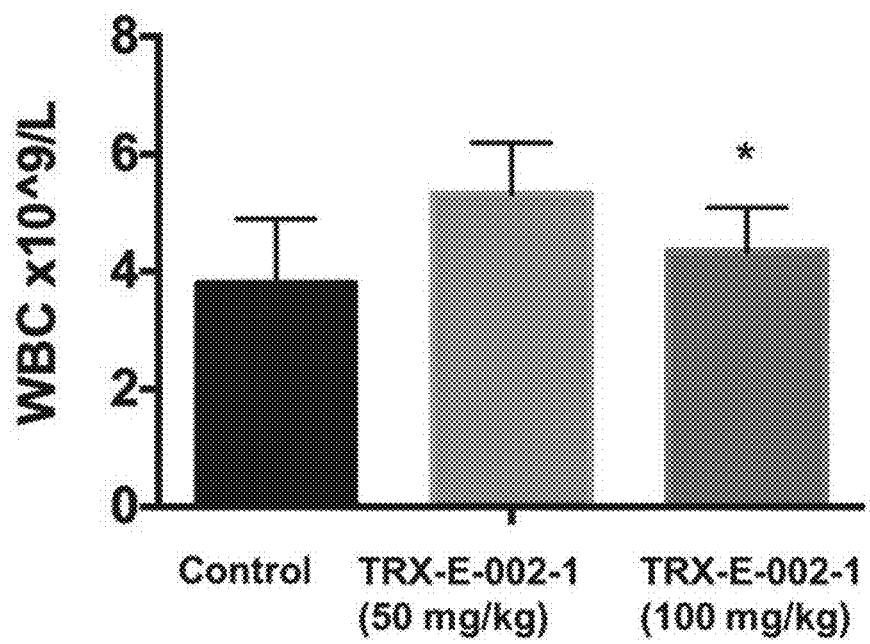

To determine activity against primary disease as well as to determine the maximum tolerated dose (MTD), a dose response study was performed. Mice receiving 150 mg/kg TRX-E-002-1 given i.p. three times weekly showed a significant decrease in tumor burden by the $10^{th}$ dose but response was accompanied by signs of toxicity (i.e. decrease mobility, weight loss, and neutropenia (FIGS. 7A-7F). In contrast, the lower doses of 50 mg/kg and 100 mg/kg given daily i.p. maintained the compound's efficacy without the toxicity observed at the higher dose (FIGS. 6A-6E). Thus, mice receiving 50 mg/kg TRX-E-002-1 showed a significant reduction in tumor burden compared to vehicle control starting at day 14 (p=0.0004) and mice receiving 100 mg/kg TRX-E-002-1 demonstrated significant reduction in tumor burden starting at day 10 compared to vehicle control (p<0.0001). These significant reductions in tumor burden were maintained until the end of the treatment (FIG. 6A). Measurement of residual disease at completion of the treatment showed a dose dependent effect with mice receiving daily 100 mg/kg TRX-E-002-1 demonstrating the best response and very little residual disease (p<0.0001, compared to vehicle control) (FIGS. 6B-6C). Molecular analysis of these residual tumors showed the upregulation of both p-c-Jun and total c-Jun (FIG. 6D). At this dose, neutropenia associated with the 150 mg/kg dose was not observed and only marginal weight loss took place (FIG. 6C). Although no animals required euthanasia due to morbidity, TRX-E-002-1 at 100 mg/kg daily was associated with abdominal distension, which was observed in 60% of animals at necropsy and primarily occurred in the caecal area. Animals however recovered from the distension upon cessation of treatment. These results demonstrate that TRX-E-002-1 given i.p. at 100 mg/kg daily was most efficacious and relatively well tolerated with no morbidity requiring euthanasia. Thus, the MTD was established at daily 100 mg/kg i.p. and this dose was employed for the succeeding studies employing combination treatment.

Example 9

Addition of TRX-E-002-1 to Cisplatin Improves Survival

Figure 6E:
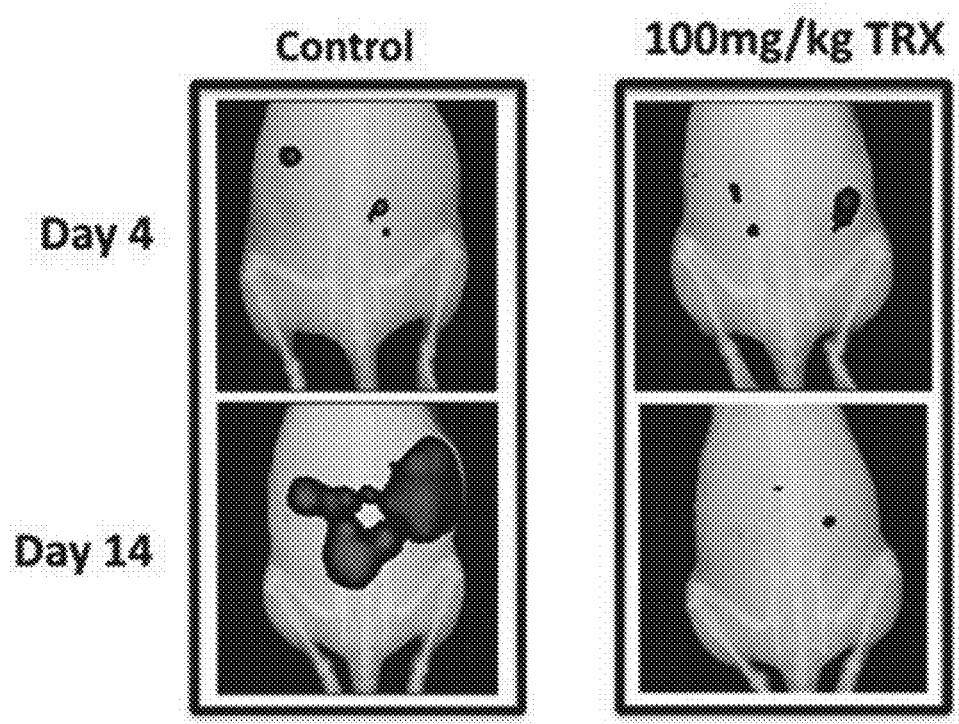

Survival of chemoresistant ovarian cancer stem cells after chemotherapy was attributed to disease recurrence and poor survival. In in vitro studies, combination of TRX-E-002-1 and Cisplatin was effective at targeting the heterogeneous cell culture comprised of chemosensitive and chemoresistant ovarian cancer cells. Thus, the value of adding TRX-E-002-1 to standard of care was determined by comparing Cisplatin monotherapy, TRX-E-002-1 monotherapy, or the combination. Animals received a total of 16 daily doses of TRX-E-002-1 (100 mg/kg) and 3 weekly doses of Cisplatin (5 mg/kg), after which animals were allowed to recover and continuously monitored. Whereas 100% of mice in the combination group were alive after 47 days post treatment, only 17-20% of animals survived in the monotherapy groups (FIG. 6E).

Example 10

TRX-E-002-1 Given as Maintenance Treatment Post Paclitaxel Delays Recurrence

Although the standard of care for ovarian cancer patients (platinum plus taxane) is effective initially, most patients develop recurrent disease. Recurrence is the major cause of mortality in ovarian cancer patients, and thus approaches that can prevent recurrence are critical to improve patient survival. As described elsewhere herein, a unique advantage of the xenograft model is the recapitulation of recurrent disease that is typically observed in patients with ovarian cancer. As such, carcinomatosis is always observed and more importantly, although animals initially respond to Paclitaxel, with some exhibiting complete response (i.e. no visible mCherry fluorescence detected by imaging), tumors eventually recur once Paclitaxel treatment is terminated. Upon recurrence, tumors acquire resistance and become unresponsive to a second-round of Paclitaxel regimen, as observed in ovarian cancer patients. Thus, the model allows one to assess the value of novel compounds in preventing recurrence when given as maintenance treatment.

Figure 6F:
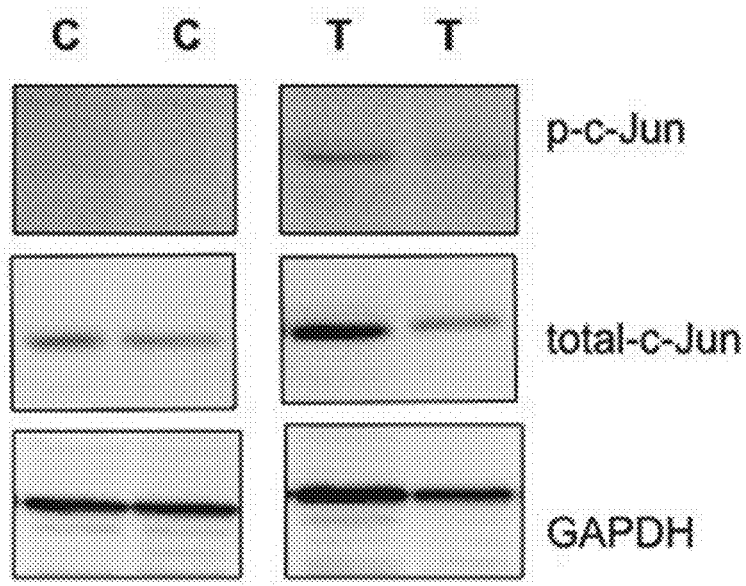
Figure 6G:
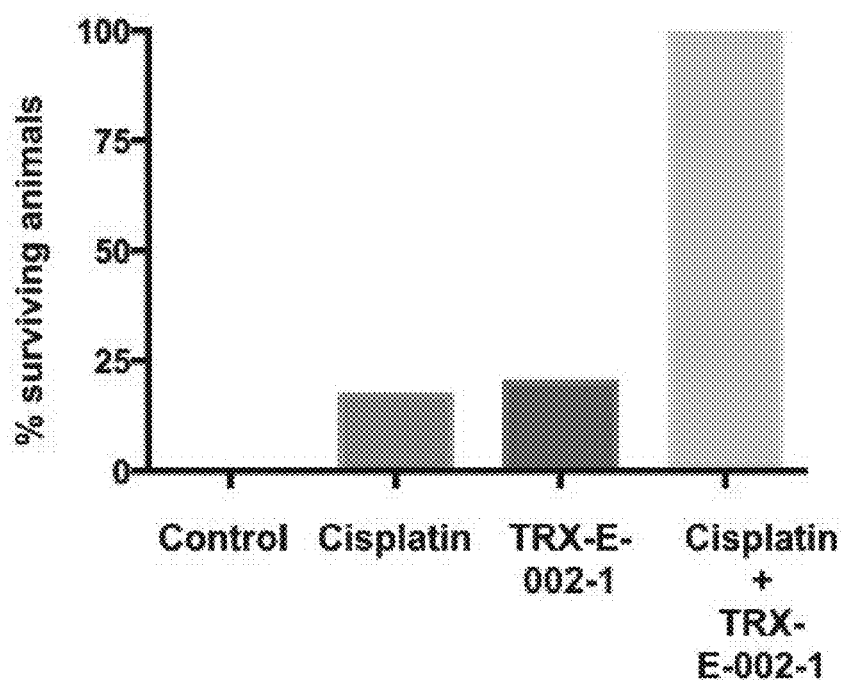
Figure 6H:
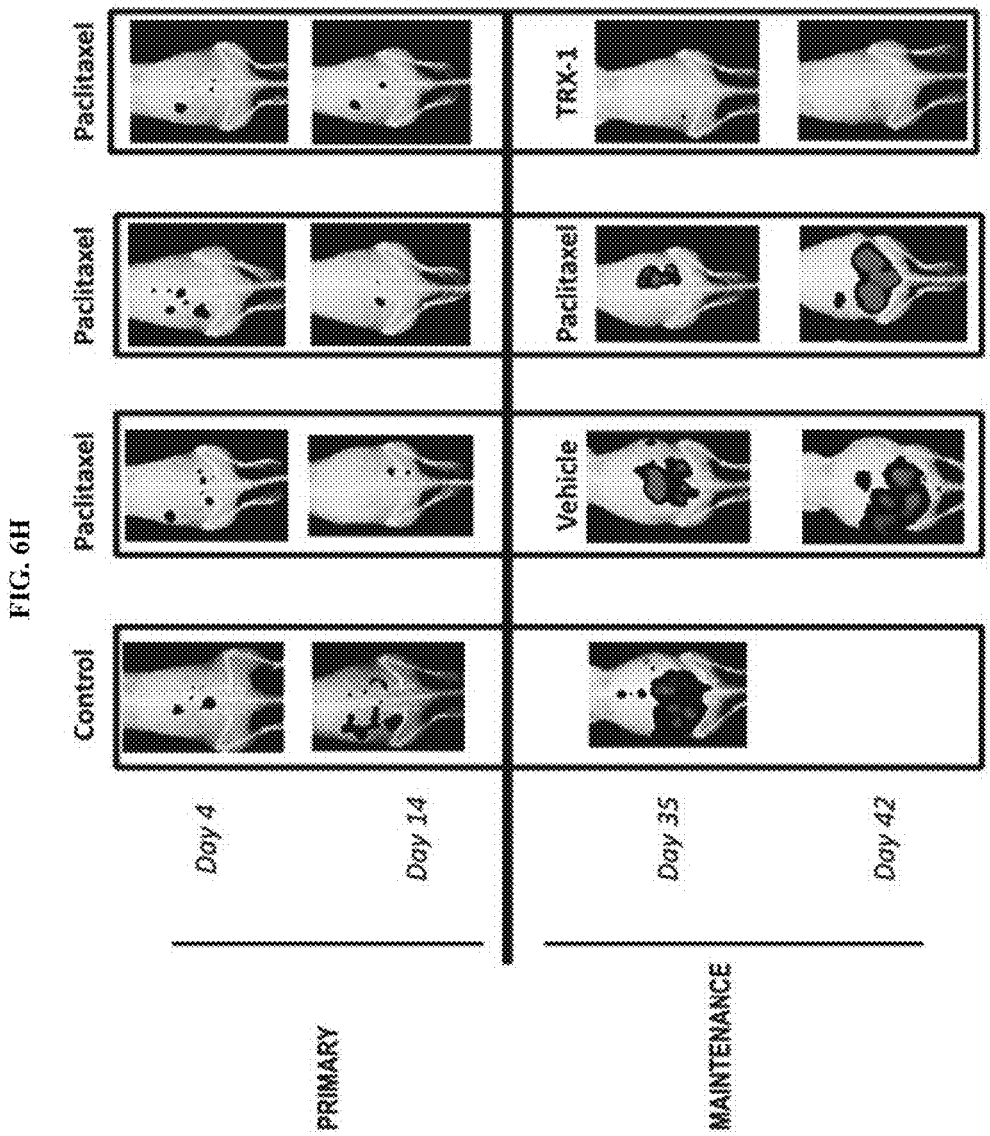
Figure 6I:
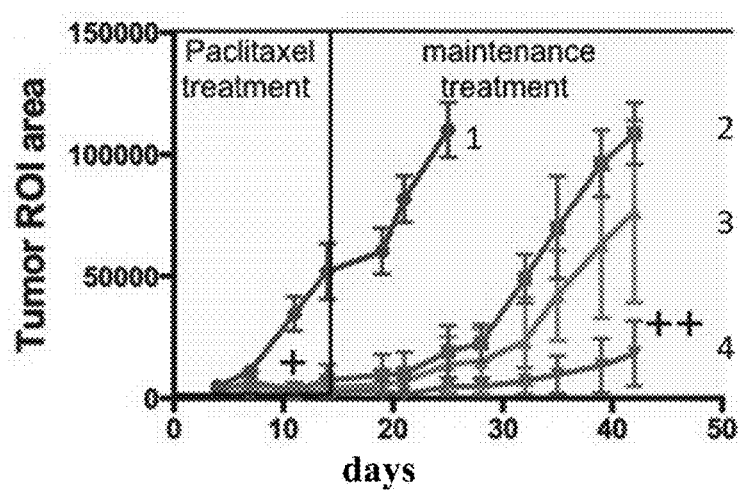
Figure 6J:
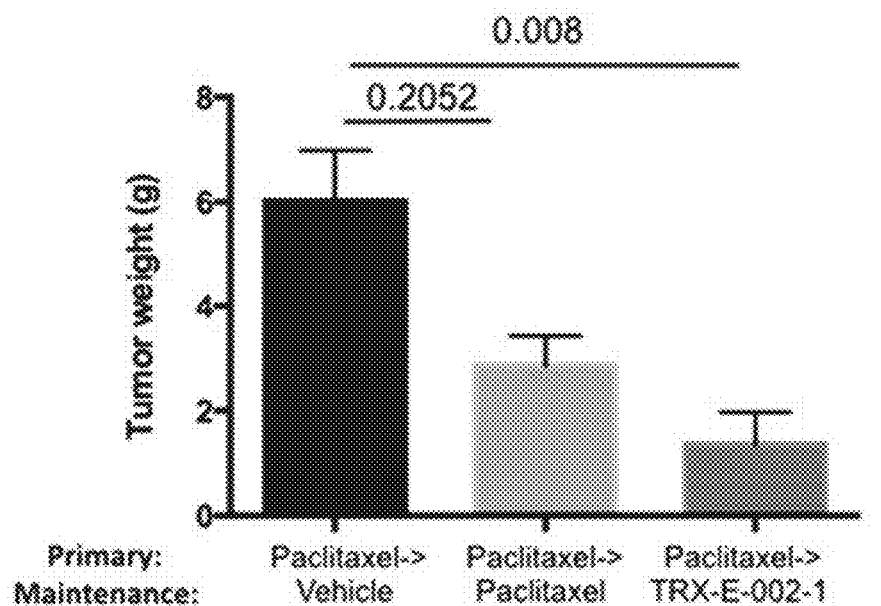
Figure 6J:
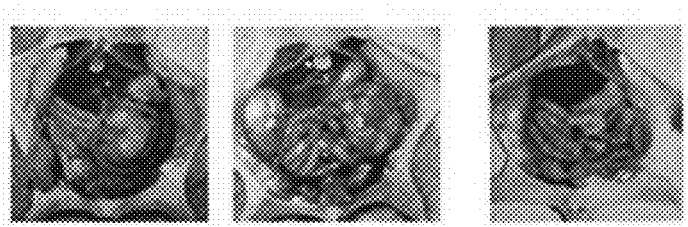
Figure 7A:
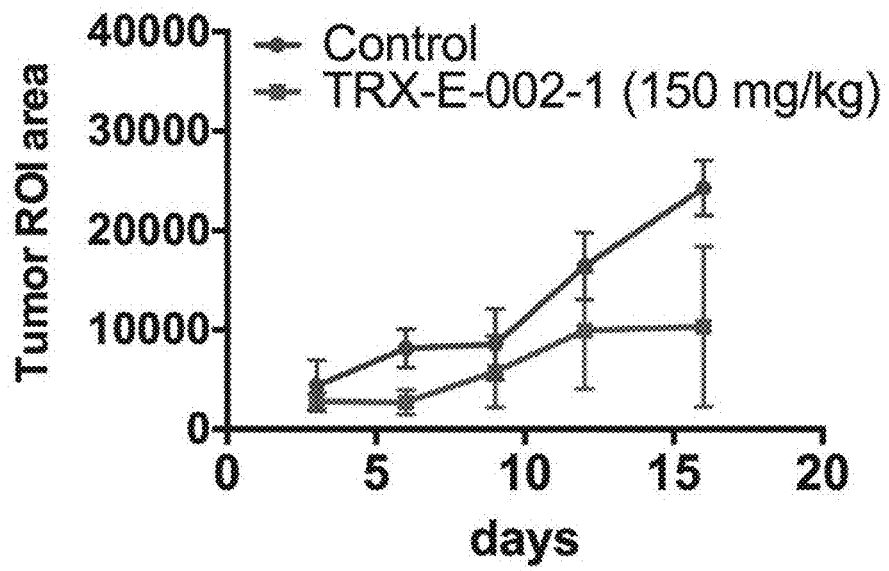
FIGS. 7A-7F illustrate findings that TRX-E-002-1 demonstrates significant anti-tumor activity in a mouse xenograft model of ovarian cancer.
Figure 7B:
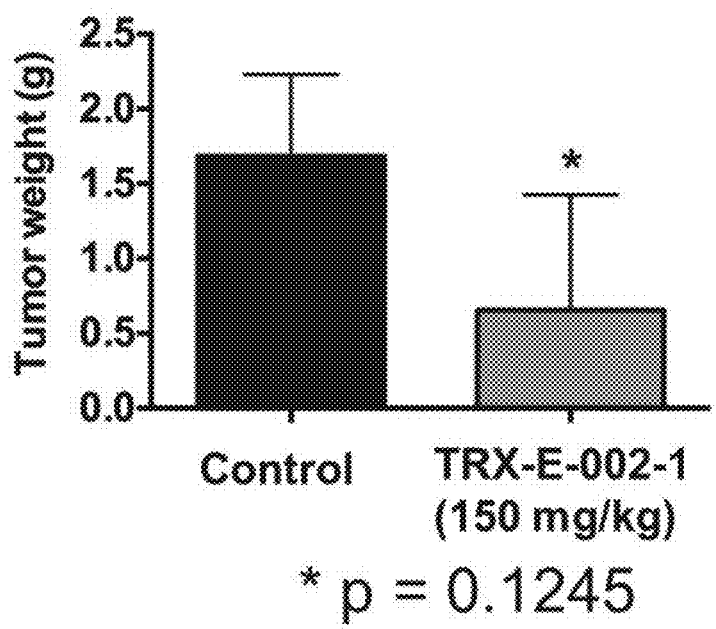
Figure 7C:
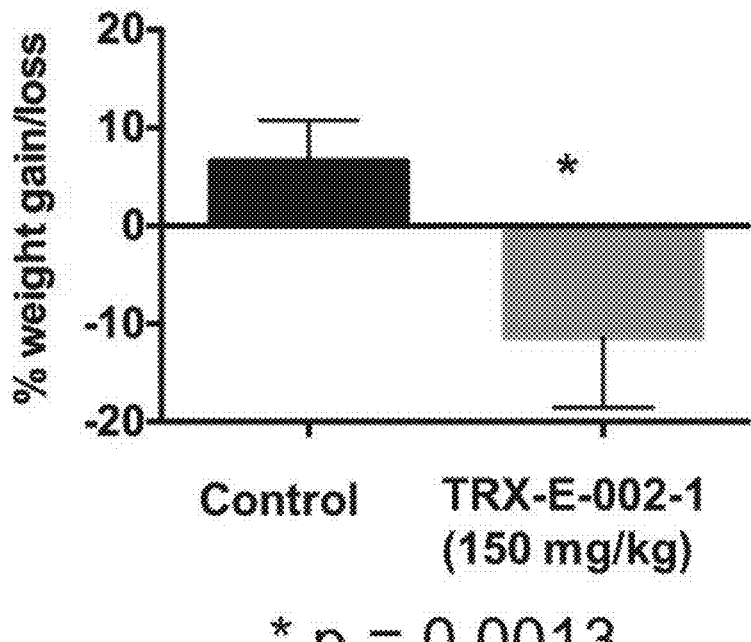
Figure 7D:
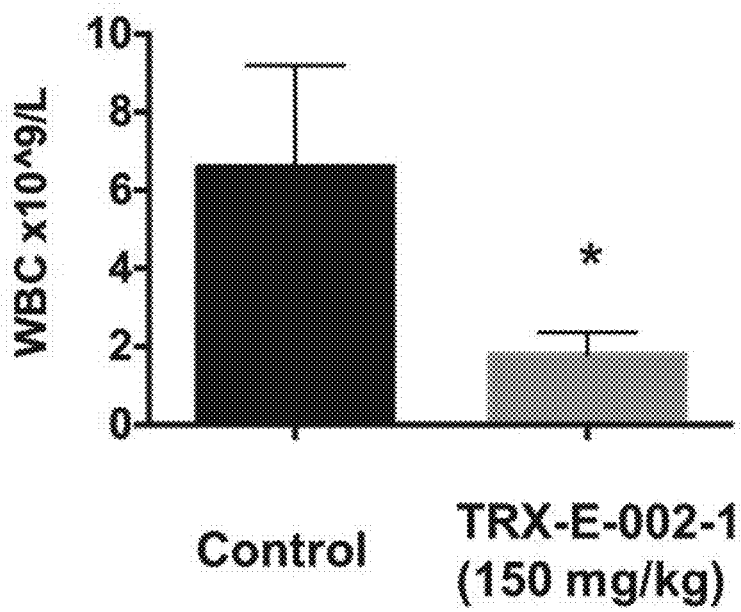
Figure 7E:
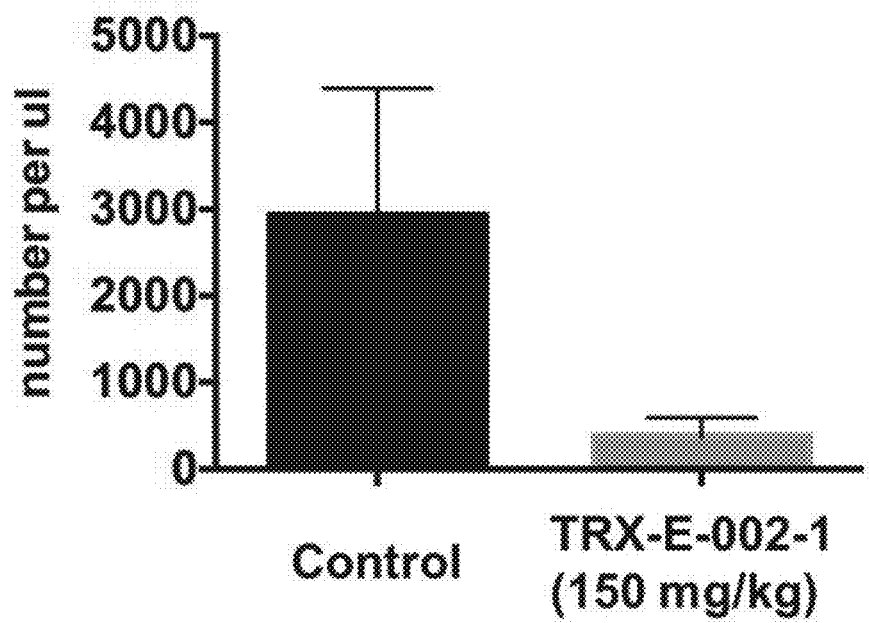
Figure 7F:
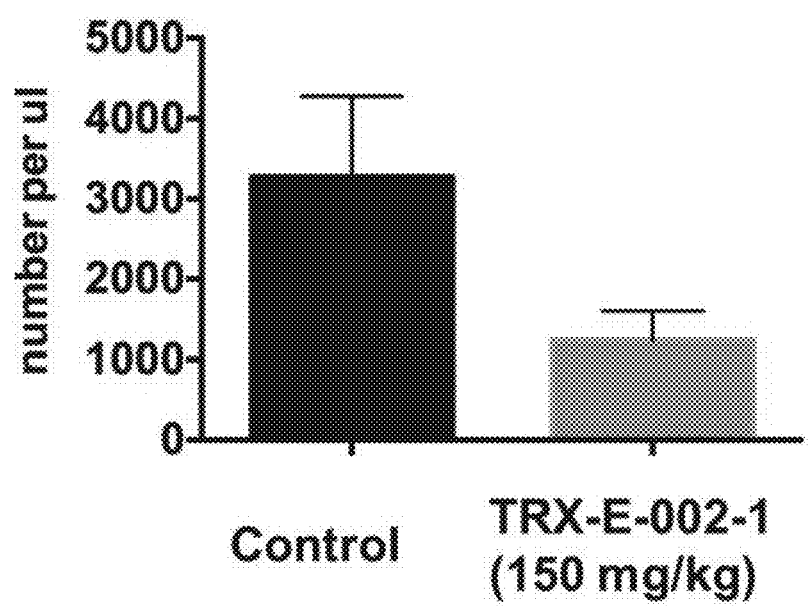

Thus mice were given Paclitaxel as initial treatment. This resulted in a significant delay in tumor progression (FIGS. 6F-6G). After the 4th dose of Paclitaxel mice were re-randomized into the different maintenance groups. Here the maintenance protocol consisted of continued treatment with Paclitaxel, or maintenance with TRX-E-002-1 (100 mg/kg), or maintenance with Vehicle control. As observed in patients who relapse with drug-resistant disease, tumor progression was observed in the group maintained with Paclitaxel indicating the tumors had acquired Paclitaxel resistance. In contrast, daily i.p. maintenance with TRX-E-002-1 effectively retarded tumor proliferation. Analysis of ROI area showed that by day 35, tumor burden in the TRX-E-002-1 maintained group was significantly less than the group maintained with Paclitaxel (p=0.003) (FIG. 6G). Tumor weights at end point were also significantly reduced in the TRX-E-002-1 maintained group compared to control (p=0.008), but not in Paclitaxel maintained group when compared to control (p=0.2052) (FIG. 6H). Gross examination of residual disease showed that mice maintained with Paclitaxel and mice maintained with vehicle had visible carcinomatosis and extensive metastasis in the diaphragm, peritoneum, and adipose tissue. In contrast, in mice maintained with TRX-E-002-1, microscopic metastasis were observed mainly in the adipose tissue. Animals appeared to tolerate this schedule of TRX-E-002-1 with no signs of disease or morbidity requiring euthanasia. Taken together, the results demonstrate the value of TRX-E-002-1 in the $1^{st}$ line setting as an addition to standard of care, and also in the maintenance setting as an adjuvant treatment after the completion of $1^{st}$ line standard of care.

Example 11

TRX-E-002-1 in Combination with an AMPK Activator Promotes Cell Death in Ovarian Cancer Stem Cells and Prevents Recurrence As demonstrated herein, the combination of TRX-E-002-1 with AICAR, an AMP kinase (AMPK) activator, induces cell death in chemoresitant ovarian cancer stem cells. AMPK is an essential kinase, which regulates energy homeostasis and cellular protection against metabolic stresses, and plays a key role in developing tolerance to nutrient starvation in some cancer cells. AMPK activation can also lead to cancer cell death when it involves the regulation of the GSK3β and Jun pathway. In a non-limiting example, combination of TRX-E-002-1 with AICAR led to cell death in chemoresistant ovarian cancer stem cells. In fact, the combination of TRX-E-002-1 and AICAR was highly effective in reducing cell number at significantly lower doses than observed with the same compounds used as monotherapy. In certain non-limiting embodiments, such combination is more effective, less toxic and/or has better activity against recurrent, chemoresistant disease than the corresponding monotherapies.

TRX-E-002-1 is very potent in inducing cell death in chemoresistant ovarian cancer stem cells, but there is evidence of some potential toxicity of this compound at high concentrations in animal studies, mainly associated with normal stem cells present in the gut and skin. Thus, drug combinations that allow to decrease TRX-E-002-1 drug concentration while maintaining its efficacy were investigated. AICAR was identified as forming a potent drug combination with TRX-E-002-1; the combination induced cell death of ovarian cancer cell cells at doses where neither compound was effective.

The effect of each compound on cell growth was assessed using a kinetic live cell imagine system (Incucyte, Essen Bioscience). Proliferation was determined based on either confluence or fluorescent count from nuclear-restricted RFP or GFP. The $IC_{50}$ values were calculated using GraphPad Prism (GraphPad Software Inc., LaJolla, Calif.). Cells were then treated with TRX-E-002-1 (25 ng/ml) or AICAR (0.2 nM) as mono therapies or in combination. FIG. 7 demonstrates that administration of either TRX-E-002-1 or AICAR as mono therapies at low concentrations had a minimal effect on cell growth of the ovarian cancer stem cells. However, the combination of the two compounds at those same concentrations had a dramatic effect on cell growth (FIG. 7).

Figure 8:
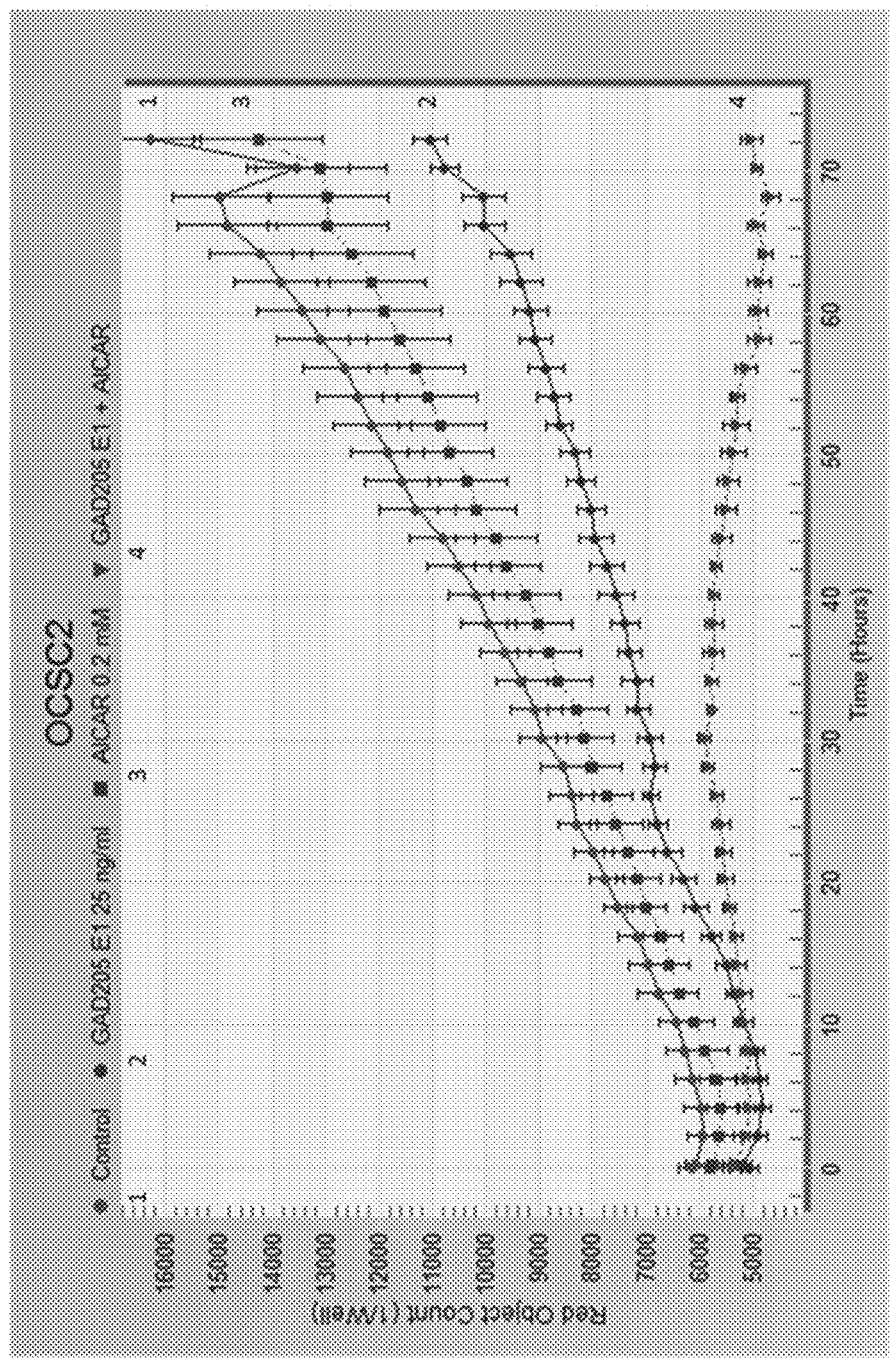
FIG. 8 illustrates cell growth of OCSCs exposed to TRX-E-002-1, AICAR as monotherapies and in combination. The combination (TRX-E-002-1+AICAR) suppressed cell growth.
Figure 9:
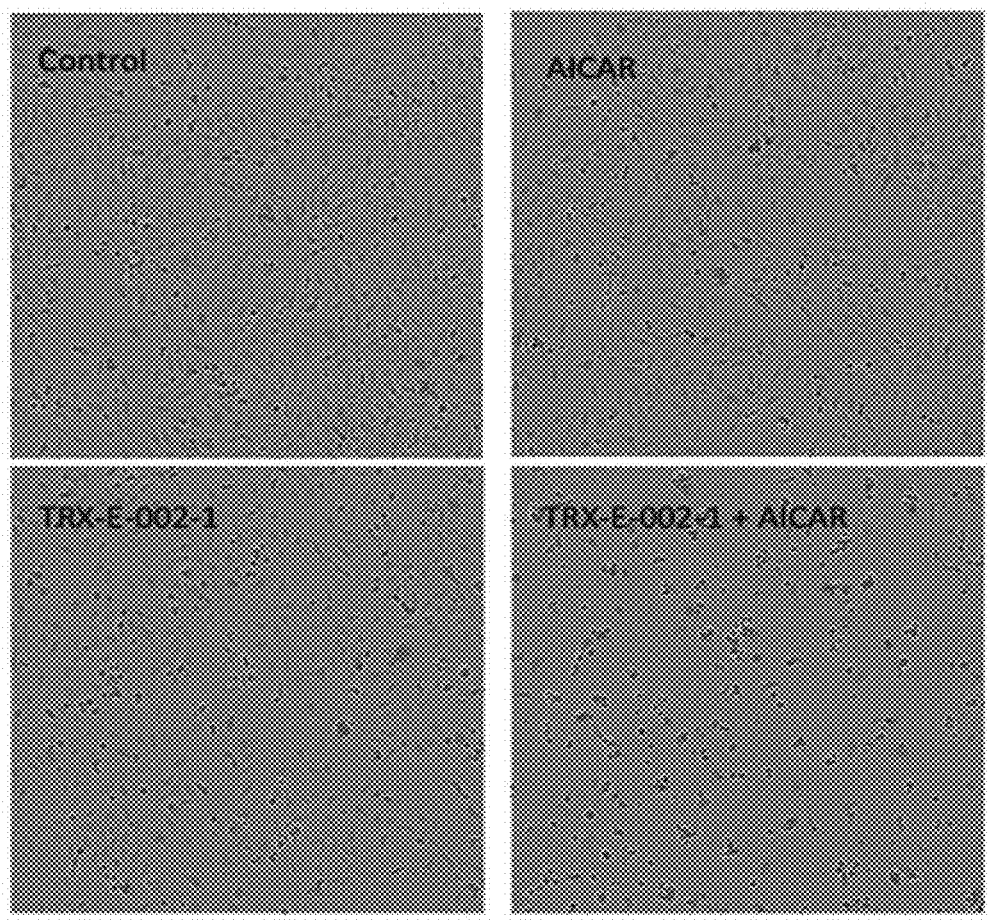
FIG. 9 depicts representative images of the morphologic characteristics of cells treated AICAR and TRX-E-002-1 as monotherapies and in combination for 48 hours of treatment.
Figure 10:
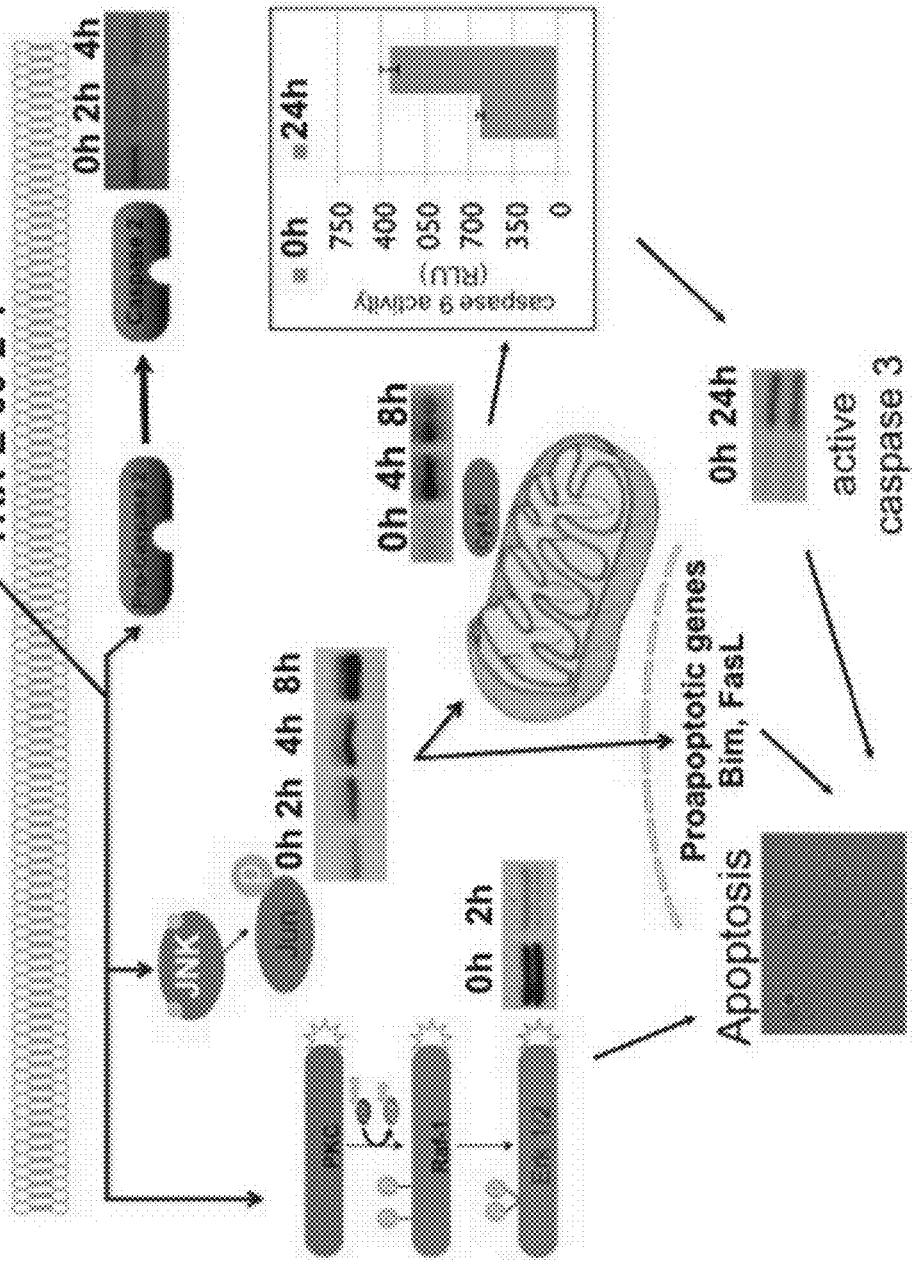
FIG. 10 illustrates a non-limiting mechanism for the biological activity of TRX-E-002-1 in vitro or in vivo. Exposure of cells (in vitro or in vivo) to that compound for a period of time (in a non-limiting example, for 2 hours) causes inhibition of c-Jun degradation. Thus, concentration of c-Jun in the cell increases, leading to accumulation of phosphorylated c-Jun (p-c-Jun), which is toxic to the cell and causes apoptosis. In certain embodiments, washing away TRX-E-002-1 from the cell after p-c-Jun has been formed does not prevent or reverse the apoptotic process.

When the morphology of the cells exposed to the different treatments were analyzed, apoptotic cells were found to be present only in the combination TRX-E-002-1 and AICAR (FIG. 8). This result confirms that the decrease in cell grow showed in FIG. 7 was due to the induction of cell death. As demonstrated in FIG. 8, AICAR at 0.2 mM concentration had no effect on the cells as compared to the control, and TRX-E-002-1 showed only minimal effect, with the presence of a few apoptotic cells (FIG. 8).

Example 12

The present studies have identified TRX-E-002-1, a SBP molecule with significant potency against relevant in vitro and in vivo models of ovarian cancer. TRX-E-002-1 was identified by screening different structural modifications on SBP against the chemoresistant OCSCs and further validating its anti-tumor activity on different ovarian cancer cell subytpes and an orthotopic ovarian cancer xenograft model. This compound mainly affects c-Jun phosphorylation and enhances expression leading to caspase activation and cell death. The efficacy was demonstrated in vivo in a highly resistant ovarian cancer animal model in the treatment of primary disease, both as monotherapy and in combination with Cisplatin. This compound has further value in maintenance therapy, wherein it is able to curtail tumor kinetics and consequently delay disease recurrence.

The survival rate in ovarian cancer has not improved since the introduction of combination chemotherapy several decades ago. Although effective in the treatment of primary disease, patients eventually recur and present with chemoresistance and carcinomatosis. Recurrence is likely caused by the re-growth of the surviving inherently chemoresistant cancer stem cells that persisted during chemotherapy. The expansion of this chemoresistant cancer cell population, coupled with pro-survival modifications induced by the pressure of treatment, is thought to be responsible for the development of chemoresistant recurrent disease. Heterogeneity of ovarian tumors is not only limited to the presence of different epithelial cell subtypes with differential steaminess potential, but also in the presence of different cancer cells with varying stages of mesenchymal status and migratory/invasiveness potential. Thus, to improve survival, a practical approach is the use of novel therapies that can induce cell death in these various subtypes of ovarian cancer cells. Indeed, TRX-E-002-1 induces cell death in chemoresistant CD44+/MyD88+OCSC clones as well as in chemosensitive CD44−/MyD88− OCC lines, both when grown separately or in co-cultures, which mimic tumor heterogeneity. Moreover, TRX-E-002-1 is potent against ovarian cancer cell spheroids and induces fragmentation of these 3D cultures.

The ovarian cancer xenograft model used in the present study recapitulates the clinical profile observed in patients, such as carcinomatosis and the initial responsiveness to chemotherapy with subsequent presentation of chemoresistant recurrent disease. As part of first line treatment, TRX-E-002-1 is efficacious when given as a monotherapy and as part of combination treatment, is not antagonistic to current standard of care and can improve outcomes in mice. As part of maintenance therapy, TRX-E-002-1 delays recurrence when given after chemotherapy. By decreasing tumor growth kinetics in recurrent disease, TRX-E-002-1 treatment resulted in lower tumor burden, which can significantly improve surgical debulking. This is important since the capacity of surgeons to perform optimal debulking and minimize residual disease has been shown to directly correlate with survival and is the best prognostic factor in ovarian cancer.

Molecular analysis demonstrates the opposing effect of TRX-E-002-1 on the Jun pathway and the ERK pathway. Despite the high levels of baseline ERK activation, the ovarian cancer cells tested do not depend on ERK signalling for survival. Thus, although TRX-E-002-1 can significantly downregulate the levels of p-ERK, simulating ERK inhibition using a MEK inhibitor did not lead to cell death. These results have clinical implications especially in patients with low-grade serous ovarian cancer wherein the Ras/Raf pathway is mutated. Without wishing to be limited by any theory, these mutations, or any other epigenetic changes that can lead to elevated baseline levels of p-ERK, may not necessarily be significant drivers of the disease.

TRX-E-002-1-induced cell death instead is associated with the persistent activation and enhanced expression levels of c-Jun. c-Jun is involved in cellular processes as diverse as proliferation, differentiation, and death. In most cells, c-Jun is regulated by phosphorylation, which can be initiated by multiple stimuli. The eventual outcome from this wide range of inputs to c-Jun further depends on the cell type and current cellular state. To activate cell death pathways, c-Jun activation and stabilization should be persistent instead of transient. Indeed, this was observed during TRX-E-002-1-induced cell death. Phosphorylation of c-Jun occurs as early as 2 h and persisted up to 16-24 h when significant caspase activation and cell death has occurred. This is accompanied by steady increase in the levels of total c-Jun, which may be a combination of transcription/translation of new protein and stabilization of already occurring c-Jun proteins.

TRX-E-002-1 can persistently activate c-Jun even when cells are exposed for only a short period of time. In cells treated with 2.45 µM of TRX-E-002-1 for 2 h and allowed to recover in growth media, phosphorylation of c-Jun as well as total levels of c-Jun steadily increased. This suggests the value of c-Jun as a biomarker for response. Indeed, c-Jun phosphorylation can be detected in vivo.

The present studies describe a complete pre-clinical study for the use of TRX-E-002-1 in ovarian cancer. The compound can fill the current need for better therapeutic options in the control and management of recurrent ovarian cancer and can help improve patient survival.

The disclosures of each and every patent, patent application, and publication cited herein are hereby incorporated herein by reference in their entirety. While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of treating ovarian epithelial cancer in a subject suffering from the cancer, wherein the ovarian epithelial cancer comprises at least one selected from the group consisting of a CD44+/MyD88+ ovarian cancer stem cell and CD44−/MyD88− ovarian cancer cell, the method comprising administering to the subject in need thereof a therapeutically effective amount of the eutomeric isomer of the compound of formula (I), which is 3-(4-hydroxy-3,5-dimethoxyphenyl)-4-(4-hydroxyphenyl)-8-methylchroman-7-ol, or a salt or solvate thereof:

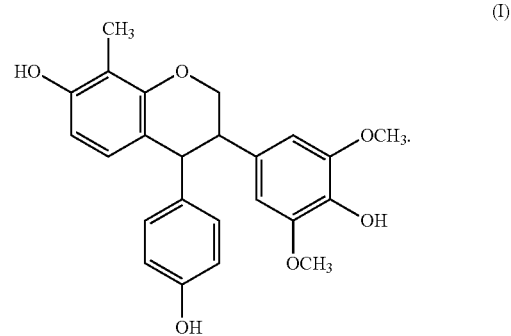 [SMILES: COc1cc(C2COc3c(ccc(O)c3C)C2c2ccc(O)cc2)cc(OC)c1O]

(I)

2. The method of claim 1, wherein the compound is at least one selected from the group consisting of: (3S,4R)-3-(4-hydroxy-3,5-dimethoxyphenyl)-4-(4-hydroxyphenyl)-8-methylchroman-7-ol; (3R,4S)-3-(4-hydroxy-3,5-dimethoxyphenyl)-4-(4-hydroxyphenyl)-8-methylchroman-7-ol ; (3 S,4 S)-3 -(4-hydroxy-3 ,5 -dimethoxyphenyl)-4-(4-hydroxyphenyl)-8-methylchroman-7-ol; and (3R,4R)-3-(4-hydroxy-3,5-dimethoxyphenyl)-4-(4-hydroxyphenyl)-8-methylchroman-7-ol.

3. The method of claim 1, further comprising administering to the subject a therapeutically effective amount of at least one agent selected from the group consisting of an adenosine monophosphate-dependent protein kinase (AMPK) activator, chemotherapeutic drug, or any salt, solvate, enantiomer, diastereoisomer, or tautomer thereof.

4. The method of claim 3, wherein the amount of the compound and the amount of the at least one agent administered to the subject are such that at least one of the following applies: (a) administration of the amount of the compound is not therapeutically effective in treating the ovarian epithelial cancer in the absence of co-administration of the amount of the at least one agent; and (b) administration of the amount of the at least one agent is not therapeutically effective in treating the ovarian epithelial cancer in the absence of co-administration of the amount of the compound.

5. The method of claim 3, wherein the subject experiences an improved disease outcome when administered the compound and the at least one agent, as compared to the disease outcome when the subject is administered the compound in the absence of the at least one agent or when the subject is administered the at least one agent in the absence of the compound, wherein the disease outcome is at least one selected from the group consisting of survival rate increase, tumor size reduction, and metastatic proliferation reduction.

6. The method of claim 3, wherein the chemotherapeutic drug is at least one selected from the group consisting of Paclitaxel, Cisplatin, Carboplatin, Topotican, and Doxoribicin.

7. The method of claim 3, wherein the adenosine monophosphate-dependent protein kinase (AMPK) activator is at least one selected from the group consisting of 5-Aminoimidazole-4-carboxamide-1-β-D-ribofuranoside (AICAR), metformin, and 5-[3-[4-[2-(4-fluorophenyl)ethoxy]phenyl]propyl]-2-furancarboxylic acid.

8. The method of claim 3, wherein the at least one agent is coformulated with the compound.

9. The method of claim 1, wherein the subject is administered the compound as part of a maintenance treatment after having been treated with at least one chemotherapy.

10. The method of claim 9, wherein the subject has suffered at least one ovarian cancer recurrence.

11. The method of claim 1, wherein the compound is administered to the subject (i) once per day, and every week day; or (ii) once per day, and five days out of every seven week days, with two consecutive rest days wherein the compound is not administered to the subject.

12. The method of claim 9, wherein the maintenance treatment prevents or delays in the subject at least one selected from the group consisting of epithelial cancer recurrence and epithelial cancer metastasis.

13. The method of claim 1, wherein the compound is formulated in a pharmaceutical composition as part of a nanoparticle, which is optionally coated with a peptide comprising ArgGlyAsp.

14. The method of claim 1, wherein the ovarian epithelial cancer is at least one selected from the group consisting of recurring and resistant to at least one chemotherapy.

* * * * *